(12) United States Patent
Tybinkowski et al.

(10) Patent No.: US 7,736,056 B2
(45) Date of Patent: Jun. 15, 2010

(54) X-RAY TRANSPARENT BED AND GURNEY EXTENDER FOR USE WITH MOBILE COMPUTERIZED TOMOGRAPHY (CT) IMAGING SYSTEMS

(75) Inventors: Andrew P. Tybinkowski, Boxford, MA (US); Lidia Nemirovsky, Salem, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

(21) Appl. No.: 11/803,241

(22) Filed: May 14, 2007

(65) Prior Publication Data

US 2008/0005844 A1   Jan. 10, 2008

Related U.S. Application Data

(63) Continuation-in-part of application No. 11/706,133, filed on Feb. 13, 2007, which is a continuation of application No. 11/193,941, filed on Jul. 29, 2005, now Pat. No. 7,175,347.

(60) Provisional application No. 60/670,164, filed on Apr. 11, 2005, provisional application No. 60/593,001, filed on Jul. 30, 2004, provisional application No. 60/800,107, filed on May 12, 2006.

(51) Int. Cl.
*A61B 6/04* (2006.01)
*A61B 6/00* (2006.01)
*H05G 1/00* (2006.01)

(52) U.S. Cl. .................... 378/209; 378/208; 378/20

(58) Field of Classification Search .................. 378/4, 378/20, 208, 195; 5/600, 601, 622
See application file for complete search history.

(56) References Cited

U.S. PATENT DOCUMENTS

| | | | |
|---|---|---|---|
| 3,603,975 | A | 9/1971 | Gordon |
| 5,448,607 | A | 9/1995 | McKenna |
| 5,887,047 | A | 3/1999 | Bailey et al. |
| 5,982,843 | A | 11/1999 | Bailey et al. |
| 6,108,396 | A | 8/2000 | Bechwati et al. |
| 6,199,233 | B1 * | 3/2001 | Kantrowitz et al. ............ 5/601 |
| 6,212,251 | B1 | 4/2001 | Tomura et al. |
| 6,217,214 | B1 | 4/2001 | Cabral et al. |
| 6,256,404 | B1 | 7/2001 | Gordon et al. |
| 6,285,028 | B1 | 9/2001 | Yamakawa |
| 6,374,937 | B1 | 4/2002 | Galando et al. |
| 6,396,902 | B2 | 5/2002 | Tybinkowski et al. |
| 6,459,923 | B1 | 10/2002 | Plewes et al. |
| 6,813,374 | B1 | 11/2004 | Karimi et al. |
| 6,857,778 | B2 | 2/2005 | Mun et al. |
| 6,926,441 | B2 | 8/2005 | Stout, Jr. |
| 6,959,068 | B1 | 10/2005 | Sommer |
| 7,319,738 | B2 | 1/2008 | Lasiuk et al. |
| 7,338,207 | B2 | 3/2008 | Gregerson et al. |

(Continued)

*Primary Examiner*—Irakli Kiknadze
(74) *Attorney, Agent, or Firm*—Pandiscio & Pandiscio

(57) ABSTRACT

A bed and gurney extender for selective attachment to a standard hospital bed or gurney for supporting the head of a patient during scanning, comprising:
 a support for supporting the head of the patient during scanning, wherein at least a portion of the support is X-ray transparent; and
 an adapter for selectively attaching the support to the bed or gurney.

30 Claims, 25 Drawing Sheets

U.S. PATENT DOCUMENTS

| | | |
|---|---|---|
| 2002/0035317 A1 | 3/2002 | Cheng et al. |
| 2002/0039403 A1 | 4/2002 | Oota |
| 2003/0095635 A1 | 5/2003 | Moritake et al. |
| 2004/0055089 A1* | 3/2004 | Dinkler et al. .................. 5/622 |
| 2005/0135560 A1* | 6/2005 | Dafni et al. .................. 378/101 |
| 2006/0083354 A1 | 4/2006 | Tybinkowski et al. |
| 2007/0183588 A1 | 8/2007 | Bailey et al. |
| 2007/0183589 A1 | 8/2007 | Tybinkowski et al. |
| 2007/0195938 A1 | 8/2007 | Bailey et al. |
| 2008/0008290 A1 | 1/2008 | Tybinkowski et al. |

* cited by examiner

X-RAY TRANSPARENT BED AND GURNEY EXTENDER FOR USE WITH MOBILE COMPUTERIZED TOMOGRAPHY (CT) IMAGING SYSTEMS

REFERENCE TO PENDING PRIOR PATENT APPLICATIONS

This patent application:

(i) is a continuation-in-part of pending prior U.S. patent application Ser. No. 11/706,133, filed Feb. 13, 2007 by Andrew P. Tybinkowski et al. for ANATOMICAL IMAGING SYSTEM WITH CENTIPEDE BELT DRIVE, which patent application is in turn a continuation of U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE BELT DRIVE, which patent application in turn claims benefit of (i) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE, and (ii) prior U.S. Provisional Patent Application Ser. No. 60/593,001, filed Jul. 30, 2004 by Bernard Gordon et al. for ANATOMICAL SCANNING SYSTEM; and (ii) claims benefit of pending prior U.S. Provisional Patent Application Ser. No. 60/800,107, filed May 12, 2006 by Andrew P. Tybinkowski et al. for X-RAY TRANSPARENT BED AND GURNEY EXTENDER FOR USE WITH MOBILE COMPUTERIZED TOMOGRAPHY (CT) IMAGING SYSTEMS.

The five above-identified patent applications are hereby incorporated herein by reference.

FIELD OF THE INVENTION

This invention relates to anatomical imaging systems in general, and more particularly to mobile Computerized Tomography (CT) imaging systems and X-ray transparent bed and gurney extenders for use with the same.

BACKGROUND OF THE INVENTION

Strokes are the third leading cause of death in the United States, causing approximately 177,000 deaths per year, and strokes are the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT scanners generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning (including non-enhanced CT scanning, CT angiography scanning and CT perfusion scanning) is able to provide substantially all of the information needed to effectively diagnose (and hence properly treat) a stroke.

Unfortunately, in practice, the CT machine is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient.

For this reason, as well as others, NeuroLogica Corporation of Danvers, Mass. has recently developed a mobile CT imaging system, i.e., the CereTom™ CT machine. The CereTom™ CT machine is particularly well suited for use in stroke applications. More particularly, the CereTom™ CT machine is a small, mobile CT machine which can be pre-positioned in the emergency room and moved to the patient so that the patient can be scanned at their current location, on their emergency room bed or gurney, thus effectively eliminating "round-trip" delays between the emergency room and radiology department and thereby dramatically reducing the time needed to properly diagnose the patient.

The CereTom™ CT machine also has application in numerous other situations where patients may be located remote from the CT machine, e.g., other hospital departments such as Intensive Care Units (ICUs), nursing homes, rehabilitation centers, etc.

Since the CereTom™ CT machine is designed to be as small and mobile as possible, and since the CereTom™ CT machine is intended primarily for stroke applications and thus need only scan the head of the patient, it is configured so as to have a relatively small-diameter scan opening, i.e., a scan opening just large enough to receive the head of the patient. Furthermore, since the beds and gurneys typically found in emergency rooms are too large to fit within the scan opening of the CereTom™ CT machine, there is an urgent need for a narrow, X-ray transparent extender for selective attachment to the bed or gurney so as to support the patient's head during scanning, whereby the patient can be quickly and easily scanned while remaining on their bed or gurney.

SUMMARY OF THE INVENTION

These and other objects of the present invention are addressed by the provision and use of a narrow, X-ray transparent extender for selective attachment to a bed or gurney so as to support a patient's head during scanning, whereby a patient can be quickly and easily scanned while remaining on their bed or gurney.

In accordance with the present invention, there is provided a bed and gurney extender for selective attachment to a standard hospital bed or gurney for supporting the head of a patient during scanning, comprising:

a support for supporting the head of the patient during scanning, wherein at least a portion of the support is X-ray transparent; and an adapter for selectively attaching the support to the bed or gurney.

In another form of the invention, there is provided apparatus for use in scanning a patient on a bed or gurney, comprising:

a bed and gurney extender for selective attachment to a standard hospital bed or gurney for supporting the head of the patient during scanning, comprising:

a support for supporting the head of the patient during scanning, wherein at least a portion of the support is X-ray transparent; and an adapter for selectively attaching the support to the bed or gurney.

In another form of the invention, there is provided a method for scanning a patient, comprising:

mounting an extender to the bed or gurney of the patient so as to present the head of the patient on an X-ray transparent support remote from the remainder of the bed or gurney;

positioning the head of the patient adjacent to the scanning zone of a scanner; and moving the scanner precisely relative to the patient during scanning while the head of the patient remains disposed on the X-ray transparent support.

In another form of the invention, there is provided a bed and gurney extender for selective attachment to a bed or gurney for supporting the head of a patient during scanning, comprising:

a support for supporting the head of the patient during scanning, wherein at least a portion of the support is transparent to the scanner; and an adapter for selectively attaching the support to the bed or gurney.

In another form of the invention, there is provided apparatus for use in scanning a patient on a bed or gurney, comprising:

a bed and gurney extender for selective attachment to a bed or gurney for supporting the head of the patient during scanning, comprising:

a support for supporting the head of the patient during scanning, wherein at least a portion of the support is transparent to the scanner; and an adapter for selectively attaching the support to the bed or gurney.

In another form of the invention, there is provided a method for scanning a patient, comprising:

mounting an extender to the bed or gurney of the patient so as to present the head of the patient on a support remote from the remainder of the bed or gurney, wherein the support is transparent to the scanner;

positioning the head of the patient adjacent to the scanning zone of a scanner; and moving the scanner precisely relative to the patient during scanning while the head of the patient remains disposed on the scanner-transparent support.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

CereTom™ CT Machine

Figure 1:
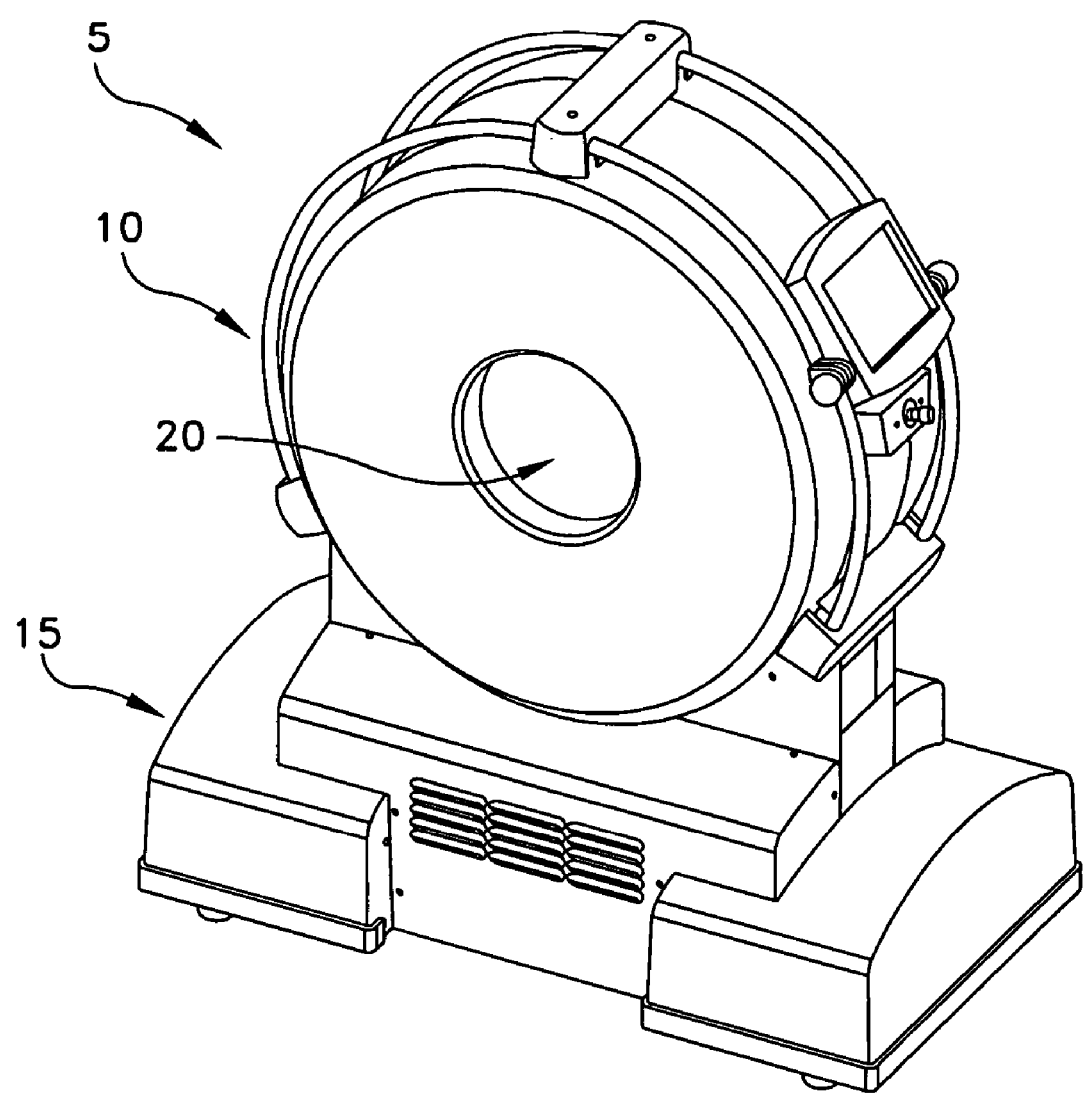
FIGS. 1 and 2 are schematic external views of a CereTom™ CT machine.
Figure 2:
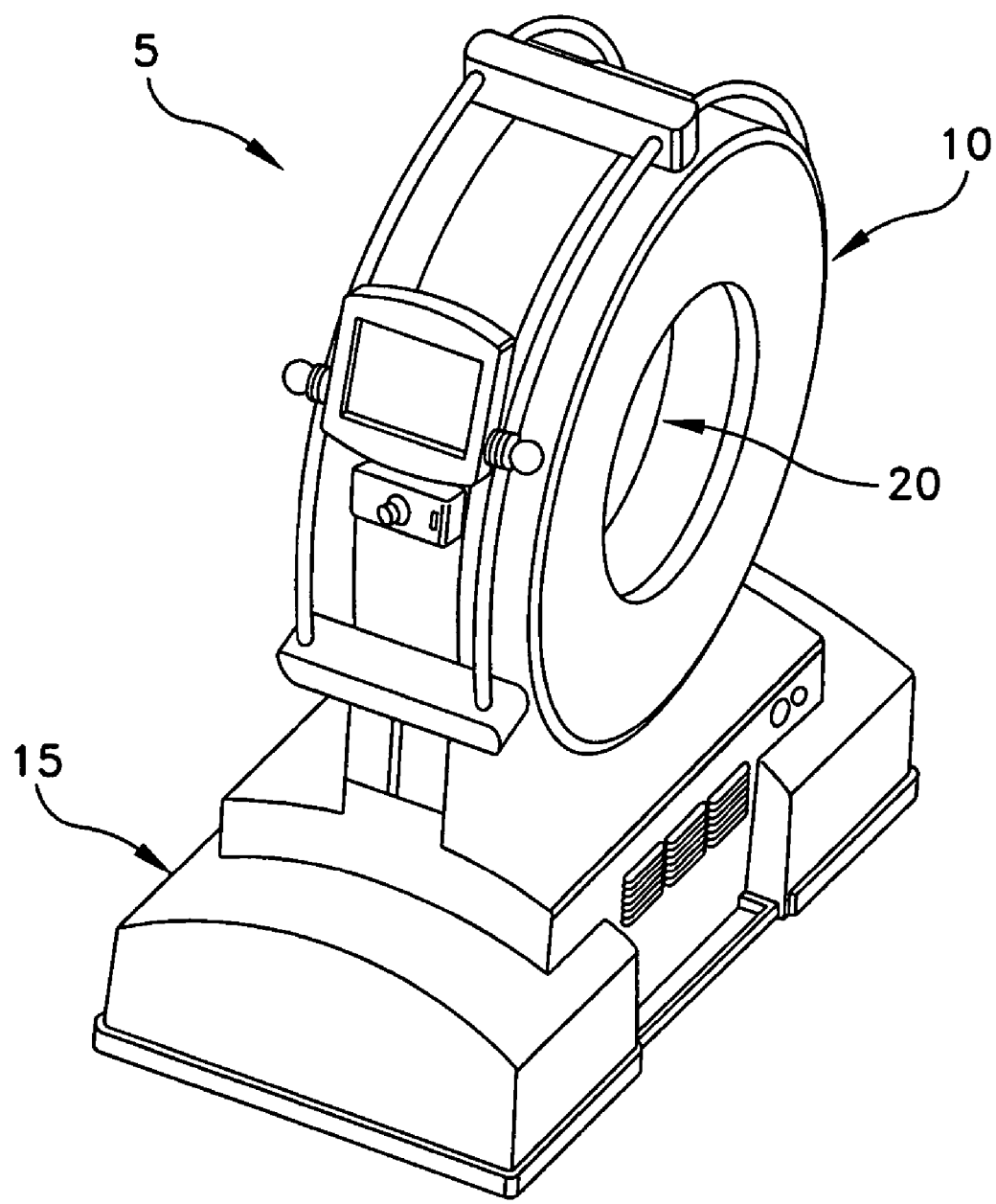

Looking first at FIGS. 1 and 2, there is shown a CereTom™ CT machine 5. CereTom™ CT machine 5 generally comprises a torus 10 which is supported by a base 15. A center opening 20 is formed in torus 10. Center opening 20 receives the patient anatomy which is to be scanned. Since CereTom™ CT machine 5 is designed to be as small and mobile as possible, and since CereTom™ CT machine 5 is intended primarily for stroke applications and thus need only scan the head of the patient, center opening 20 is configured to be just slightly larger than the head of the patient.

Figure 3:
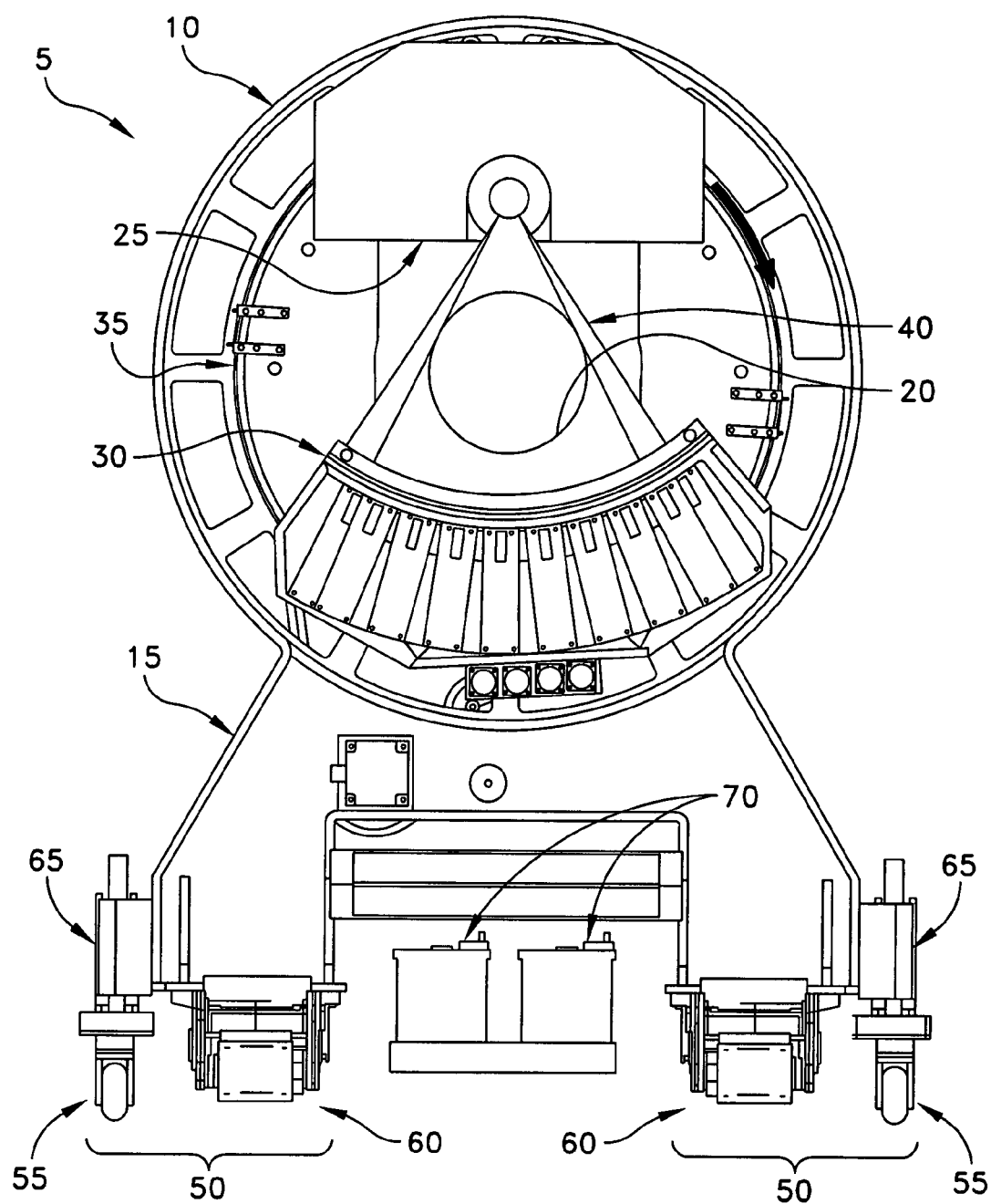
FIG. 3 is a schematic internal view of the CereTom™ CT machine shown in FIGS. 1 and 2.

Looking next at FIG. 3, torus 10 generally comprises an X-ray tube assembly 25, an X-ray detector assembly 30, and a rotating drum assembly 35. X-ray tube assembly 25 and X-ray detector assembly 30 are mounted to the rotating drum assembly 35 in diametrically-opposing relation, such that the X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on the rotating drum assembly 35 so that they are rotated concentrically about center opening 20, the X-ray beam 40 will be passed through the patient's anatomy along a full range of radial positions, so as to enable the CereTom™ CT machine to create the desired computer model of the scanned anatomy.

The various electronic hardware and software for controlling the operation of X-ray tube assembly 25, X-ray detector assembly 30, and rotating drum assembly 35, as well as for processing the acquired scan data so as to generate the desired computer model, are located in torus 10 and/or base 15.

Still looking now at FIG. 3, base 15 comprises a transport assembly 50 for moving CereTom™ CT machine 5 about relative to the patient. More particularly, as disclosed in the aforementioned U.S. patent application Ser. No. 11/706,133, which patent application is hereby incorporated herein by reference, transport assembly 50 comprises a gross movement mechanism 55 for moving CereTom™ CT machine 5 relatively quickly across room distances, and a fine movement mechanism 60 for moving CereTom™ CT machine 5 precisely, relative to the patient, during scanning. As discussed in detail in the aforementioned U.S. patent application Ser. No. 11/706,133, gross movement mechanism 55 preferably comprises a plurality of casters, and fine movement mechanism 60 preferably comprises a plurality of centipede belt drives. Hydraulic apparatus 65 permits either gross movement mechanism 55, or fine movement mechanism 60, to be engaged with the floor, whereby to facilitate appropriate movement of CereTom™ CT machine 5.

Base 15 also includes other system components in addition to those discussed above, e.g., batteries 70 for powering various electrical components of CereTom™ CT machine 5, etc.

As noted above, the various components of CereTom™ CT machine 5 are engineered so as to provide a relatively small, mobile and inexpensive CT machine.

CereTom™ CT machine 5 is particularly well suited for use in stroke applications. More particularly, CereTom™ CT machine 5 is a small, mobile unit which can be pre-positioned in the emergency room and moved to the patient so that the patient can be scanned at their current location, thus eliminating delays due to patient transport and thereby dramatically reducing the time needed to properly diagnose the patient.

More particularly, the mobile CereTom™ CT machine 5 can be located in the emergency room of a hospital and, when a patient presents stroke symptoms, the patient can be immediately scanned in the emergency room so as to determine if the patient is experiencing a stroke and, if so, to determine the nature of the stroke (i.e., hemorrhagic or ischemic). This may be done quickly and easily by moving CereTom™ CT machine 5 across the emergency room to the patient's bed or gurney using the casters of gross movement mechanism 55 and then, while the patient remains on their bed or gurney, scanning the patient by precision-advancing CereTom™ CT machine 5 relative to the patient using the centipede belt drives of fine movement mechanism 60, so that the scanning zone of CereTom™ CT machine 5 is moved relative to the patient. Thus, with CereTom™ CT machine 5, the patient can be scanned in the emergency room while remaining on their bed or gurney, without ever having to be moved from the emergency room to the radiology department and then back again, thereby eliminating the traditional scanning delays associated with conventional CT scanners and thus facilitating proper stroke treatment.

As noted above, the CereTom™ CT machine 5 also has application in numerous other situations where the patient is located remote from the CT machine, e.g., other hospital departments such as Intensive Care Units (ICUs), nursing homes, rehabilitation centers, etc.

X-Ray Transparent Bed and Gurney Extender

As noted above, CereTom™ CT machine 5 is designed to be as small and mobile as possible, and need only scan the head of the patient. As a result, CereTom™ CT machine 5 is configured so as to have a relatively small-diameter center scan opening 20 to receive the head of the patient. Since the hospital beds and gurneys typically found in emergency rooms are too large to fit within the scanning area of CereTom™ CT machine 5, the present invention provides a narrow, X-ray transparent extender for selective attachment to the bed or gurney so as to support the patient's head during scanning, whereby the patient can be quickly and easily scanned while remaining on their bed or gurney.

Figure 4:
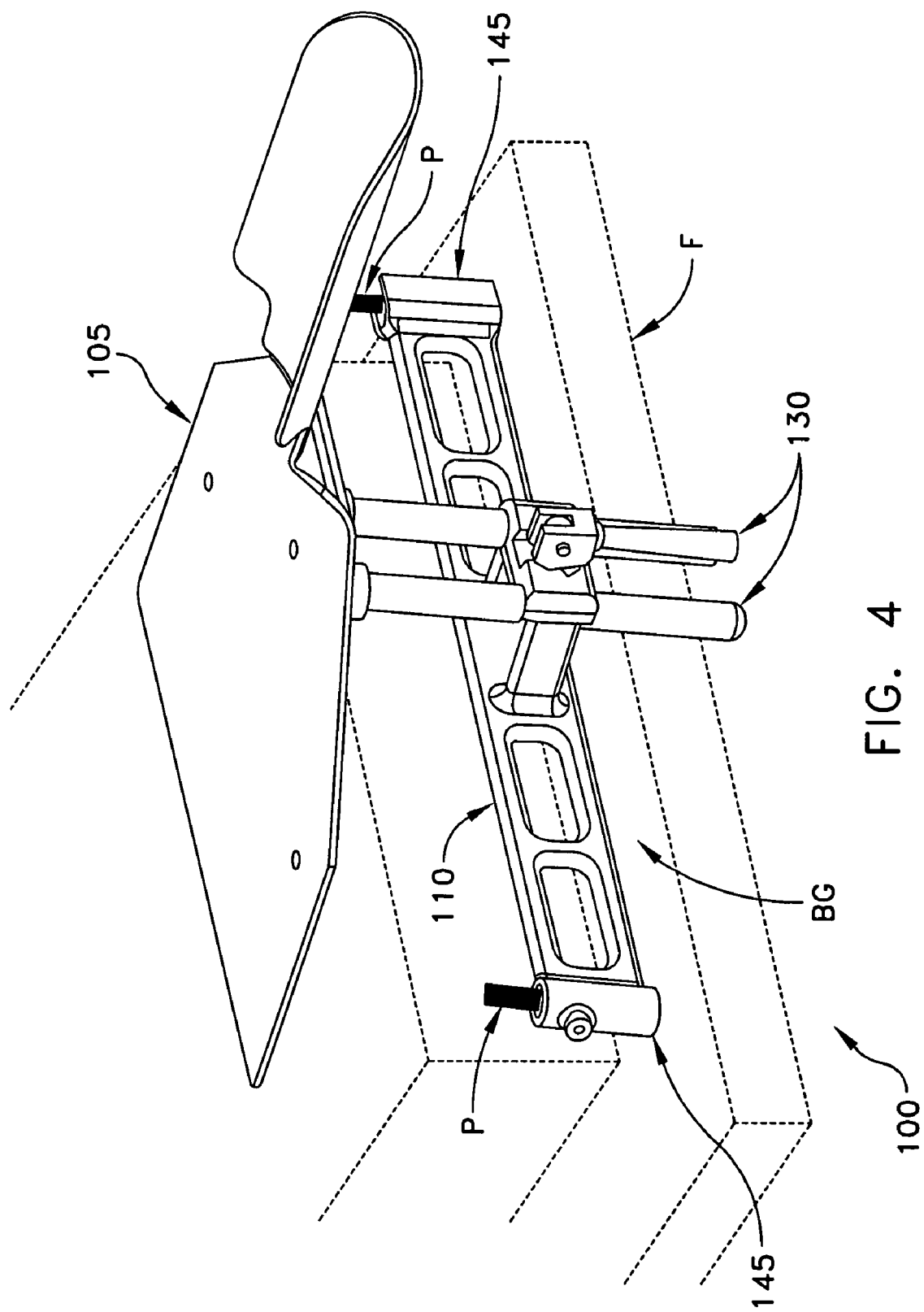
FIG. 4 is a schematic view showing a bed and gurney extender formed in accordance with the present invention.

More particularly, and looking now at FIG. 4, there is shown a bed and gurney extender 100 for selective attachment to a bed or gurney BG. For the purposes of the present invention, bed or gurney BG may be a conventional bed or gurney of the type typically found in an emergency room, or it may be any other patient-supporting platform, e.g., an examination table, an operating table, a medical reclining chair, etc.

Extender 100 generally comprises a support 105 for supporting the head of the patient during scanning, and an adapter 110 for selectively attaching support 105 to bed or gurney BG.

Figure 5:
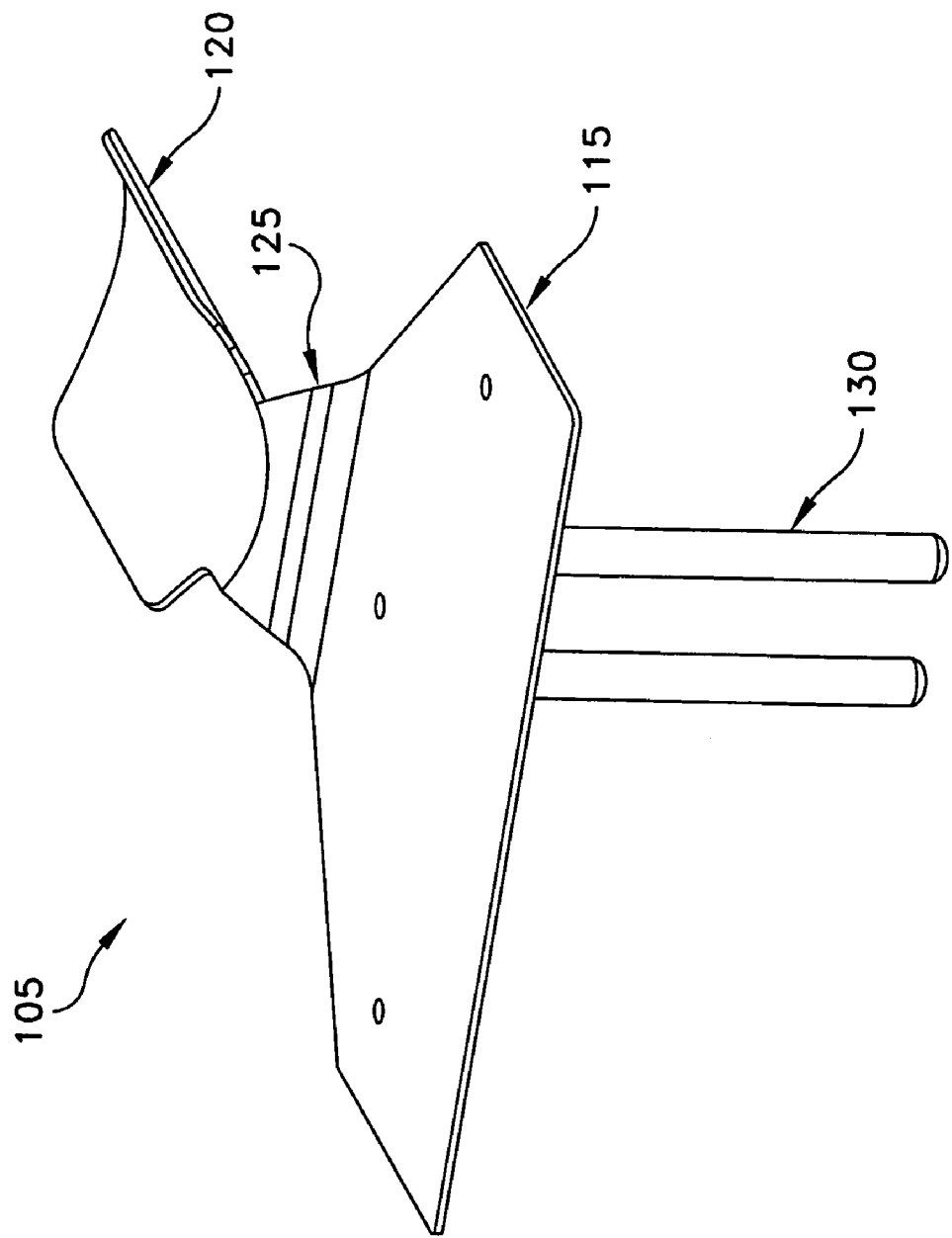
FIGS. 5 and 6 are schematic views showing the support portion of the bed and gurney extender shown in FIG. 4.
Figure 6:
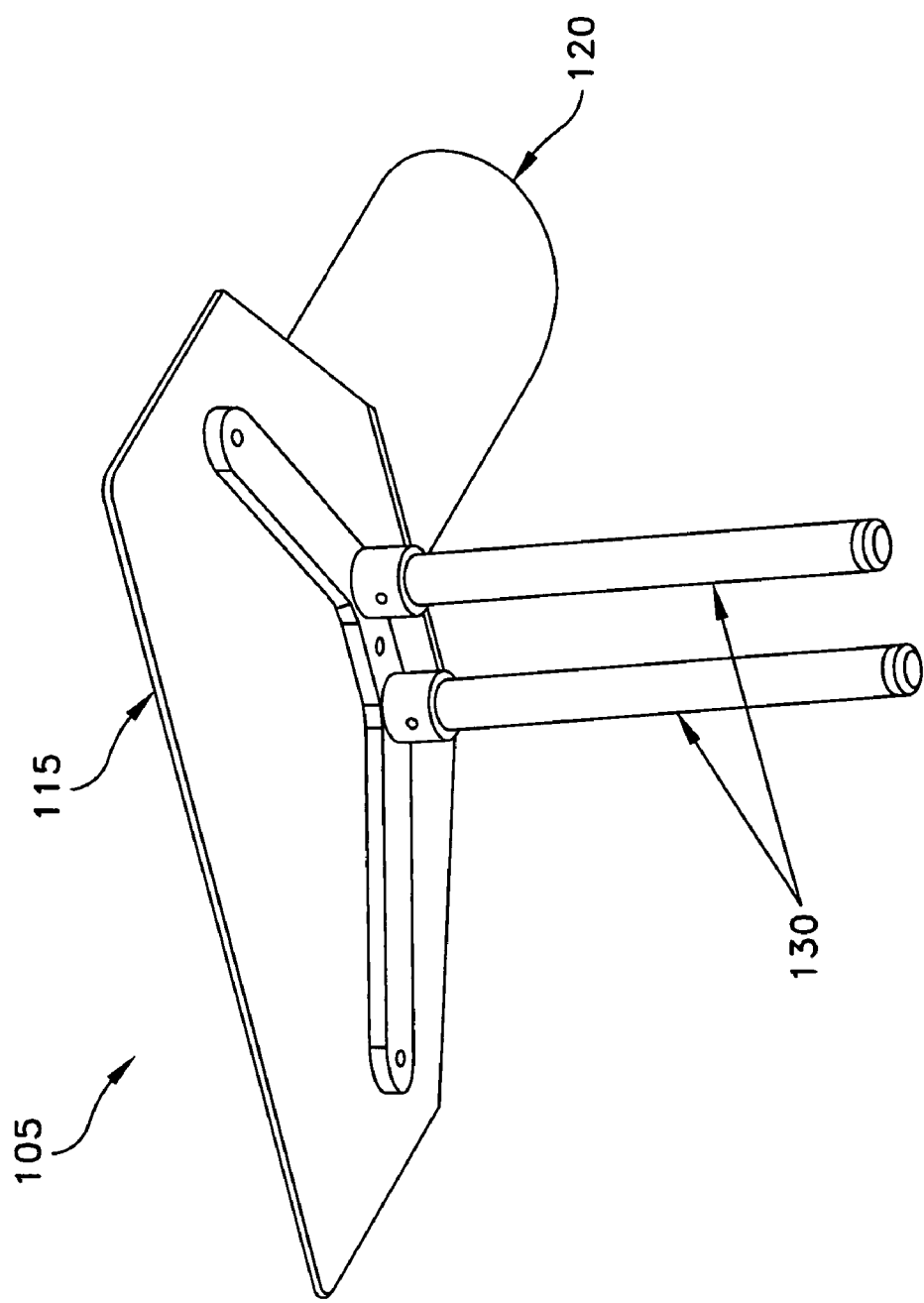
Figure 7:
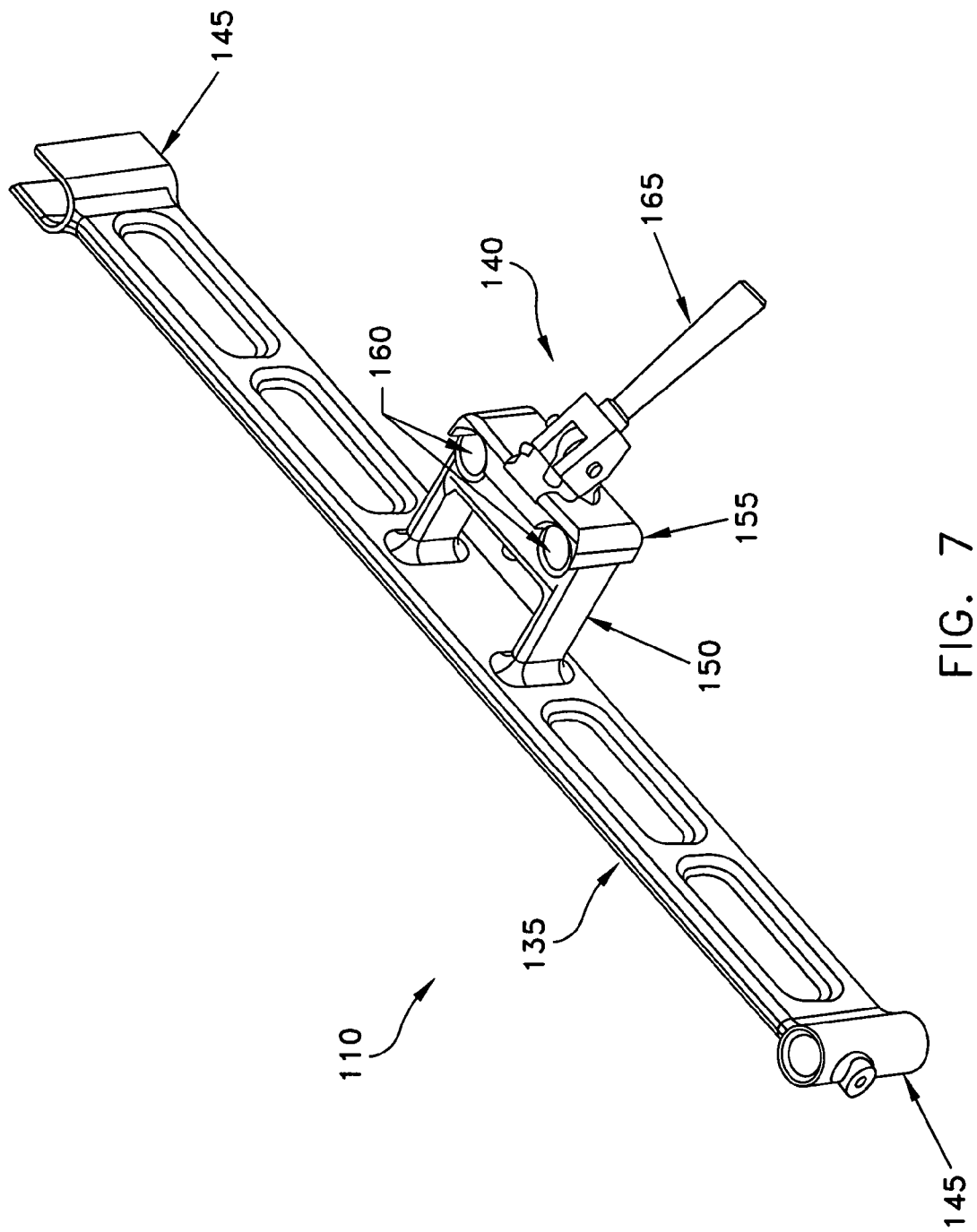
FIGS. 7-10 are schematic views showing the adapter portion of the bed and gurney extender shown in FIG. 4.
Figure 8:
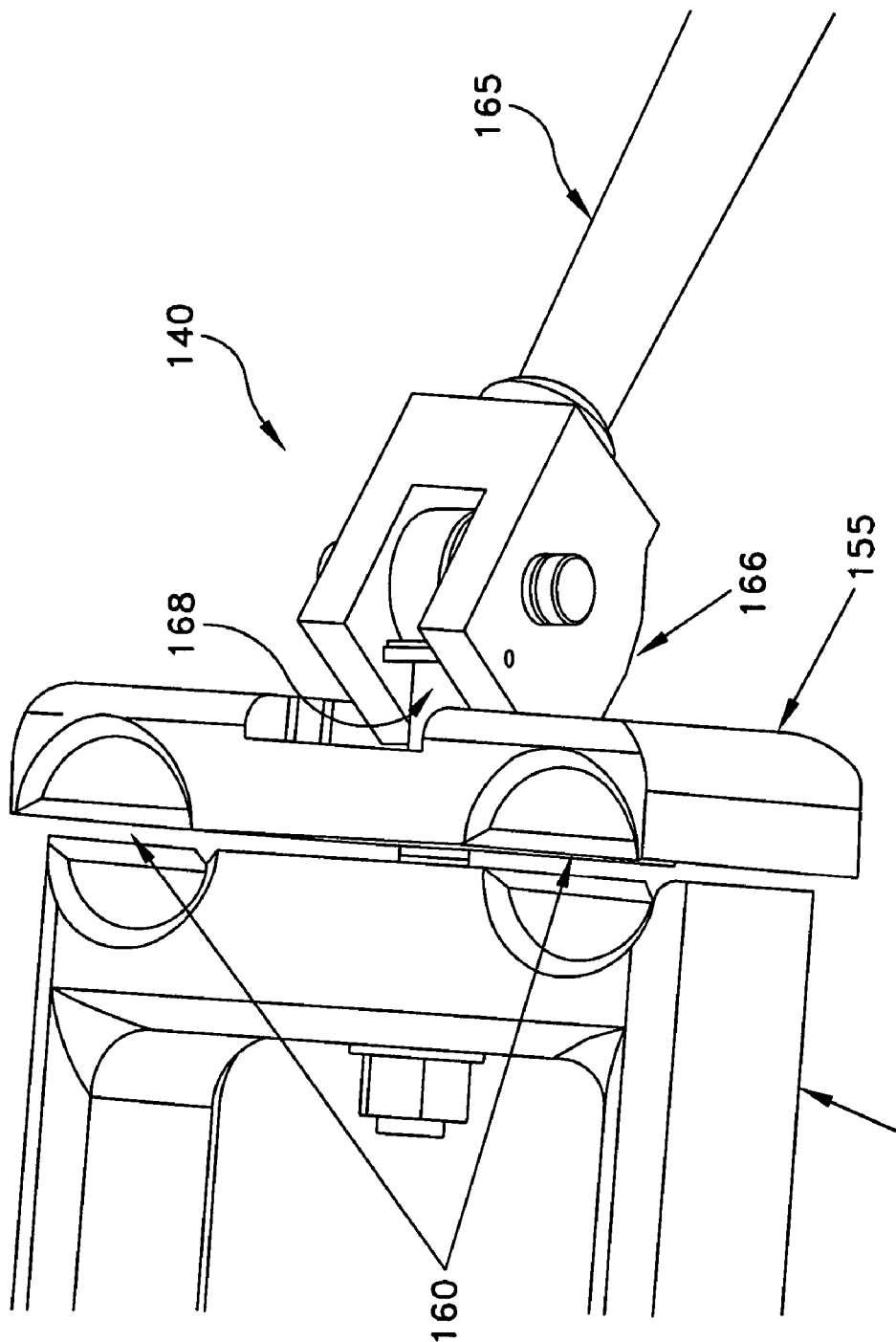
Figure 9:
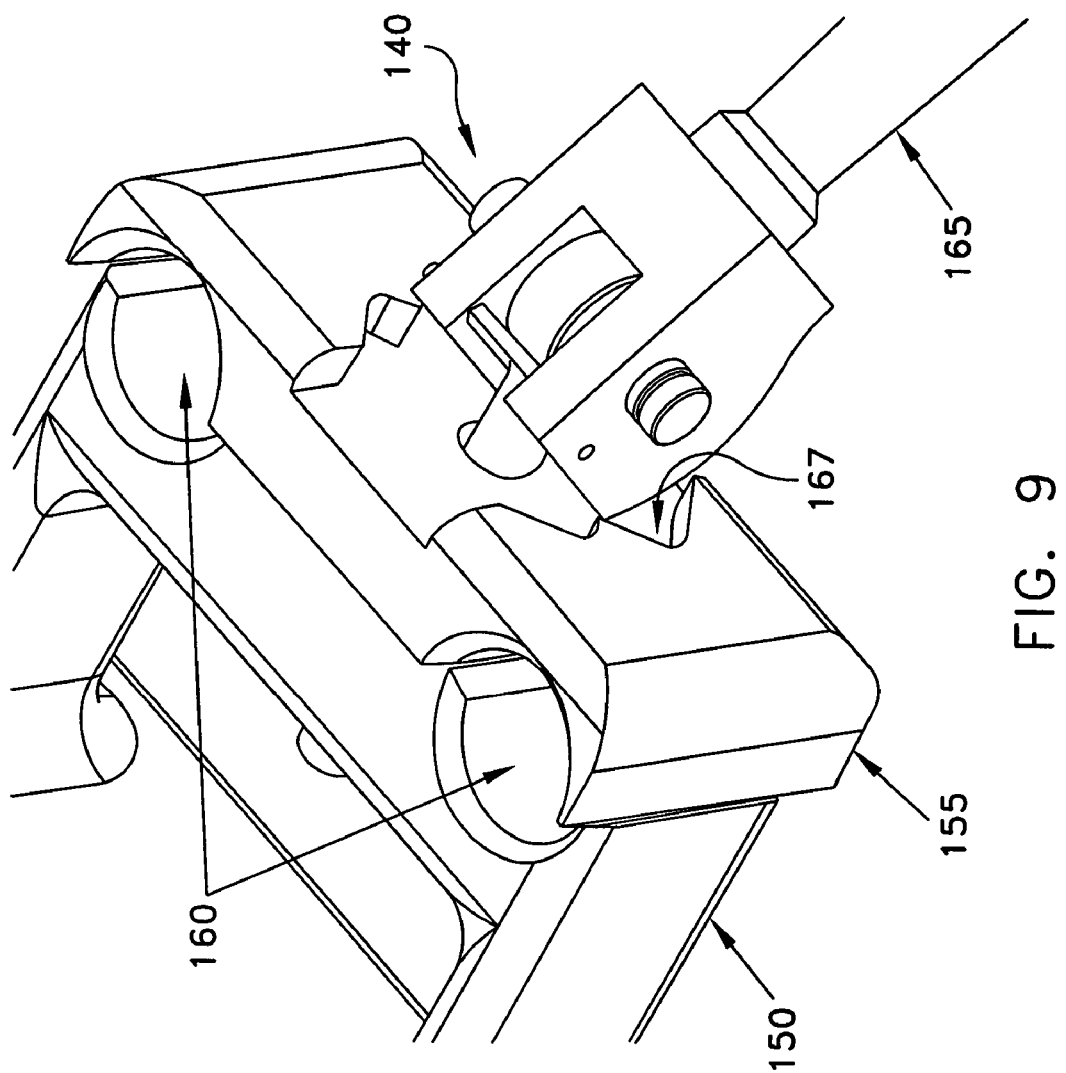
Figure 10:
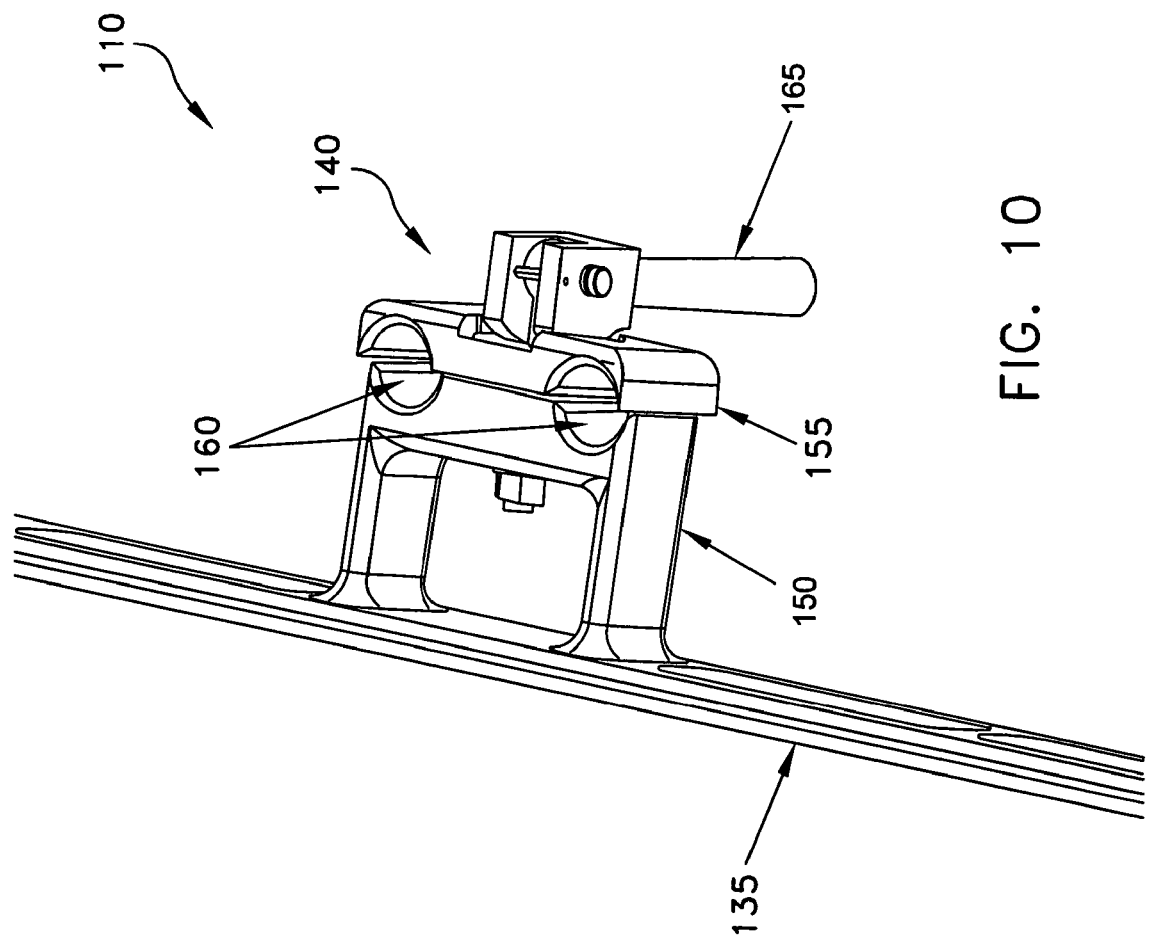

Looking next at FIGS. 5 and 6, support 105 generally comprises a shoulder section 115 for disposition on bed or gurney BG, under the shoulders of the patient, and a head section 120 for supporting the head of the patient. Preferably, head section 120 is connected to shoulder section 115 by a neck section 125.

At least head section 120 is formed out of an X-ray transparent material (e.g., carbon fiber, plastic, etc.), such that head section 120 can be in center opening 20 of CereTom™ CT machine 5 during scanning. If desired, shoulder section 115 and/or neck section 125 can also be formed out of an X-ray transparent material. At least one riser 130 extends out of the underside of shoulder section 115 for selective attachment to adapter 110. In one preferred form of the invention, two risers 130 are provided.

Adapter 110 is shown in FIGS. 4 and 7-10. Adapter 110 generally comprises a bed and gurney mount 135 for selective attachment to the bed or gurney BG, and a riser clamp 140 for selectively securing the at least one riser 130 of support 105 to adapter 110.

The specific configuration of bed and gurney mount 135 is chosen according to the specific configuration of bed or gurney BG. Thus, for example, as seen in FIG. 4, where bed or gurney BG comprises a pair of posts P upstanding from the frame F of bed or gurney BG, bed and gurney mount 135 may comprise a pair of receptacles 145 for receiving posts P, whereby to secure bed and gurney mount 135 to the bed or gurney BG.

Of course, other bed and gurney configurations exist in the marketplace, and hence other configurations may be provided for bed and gurney mount 135, with the specific configuration of bed and gurney mount 135 being matched to the particular configuration of the bed or gurney BG with which the extender 100 is to be used.

Riser clamp 140 comprises a fixed plate 150 and a movable plate 155 which together define at least one variably-sized opening 160 for selectively receiving and securing the at least one riser 130 of support 105. In one preferred form of the invention, two variably-sized openings 160 are provided for receiving the two risers 130 of support 105. In the construction shown in FIGS. 7-10, a handle 165 manipulates a cam mechanism for opening and closing riser clamp 140. In one preferred construction (FIGS. 7-10), handle 165 has a cam surface 166 which bears against plate surface 167 so as to selectively position movable plate 155 along shaft 168, whereby to open and close riser clamp 140. Thus it will be seen that when riser clamp 140 is in its open position, risers 130 can be slidably received in openings 160; and when riser clamp 140 is in its closed position, risers 130 are secured to adapter 110, whereby to secure support 105 to bed or gurney BG.

Use

The apparatus may be used as follows.

When a patient arrives at the emergency room presenting stroke-like symptoms, they are quickly scanned in the emergency room, on their bed or gurney, using CereTom™ CT machine 5 (which is pre-positioned in the emergency room) and extender 100. More particularly, CereTom™ CT machine 5 is raised on its gross movement mechanism 55, i.e., by actuating hydraulic actuators 65. CereTom™ CT machine 5 is then moved on its casters to the patient. Extender 100 is secured to the bed or gurney BG by securing adapter 110 to the bed or gurney BG, opening riser clamp 140 if it is not already open, moving risers 130 through openings 160 of riser clamp 140 until the extender's shoulder section 115 lies flat on the top surface of the bed or gurney BG (the patient may be lifted slightly to facilitate this), and then riser clamp 140 is closed, thereby securing support 105 to bed or gurney BG. Then the patient is moved as necessary so that the head of the patient lies on head section 120. Next, CereTom™ CT machine 5 (which is still raised on its casters) is moved relative to the bed or gurney BG so that the center opening 20 of CereTom™ CT machine 5 is aligned with the patient. Thereafter, hydraulic apparatus 65 is activated so that CereTom™ CT machine 5 is supported on its fine movement mechanism 60 (i.e., the centipede belt drives). Scanning is then commenced, with fine movement mechanism 60 precision-advancing (or precision-retracting, or both precision-advancing and precision-retracting) CereTom™ CT machine 5 relative to the patient during scanning, with scanning being achieved while the patient remains on their bed or gurney. As scanning occurs, head section 120 (upon which the patient's head is supported) does not inhibit scanning, inasmuch as head section 120 is formed out of an X-ray transparent material.

Storing Bed And Gurney Extender 100

Figure 11:
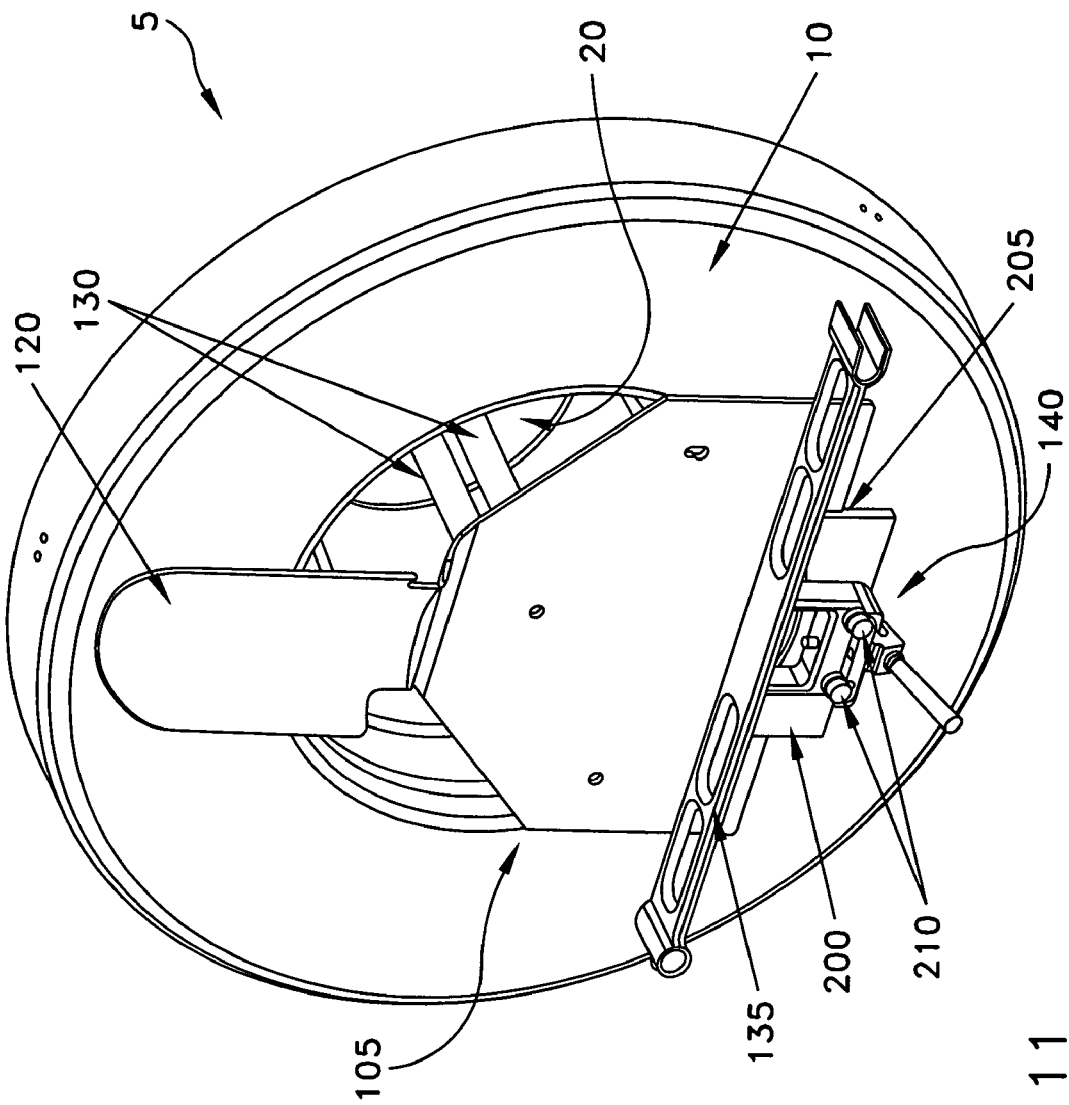
FIGS. 11-14 are schematic views showing how the bed and gurney extender may be stored on a CereTom™ CT machine.
Figure 12:
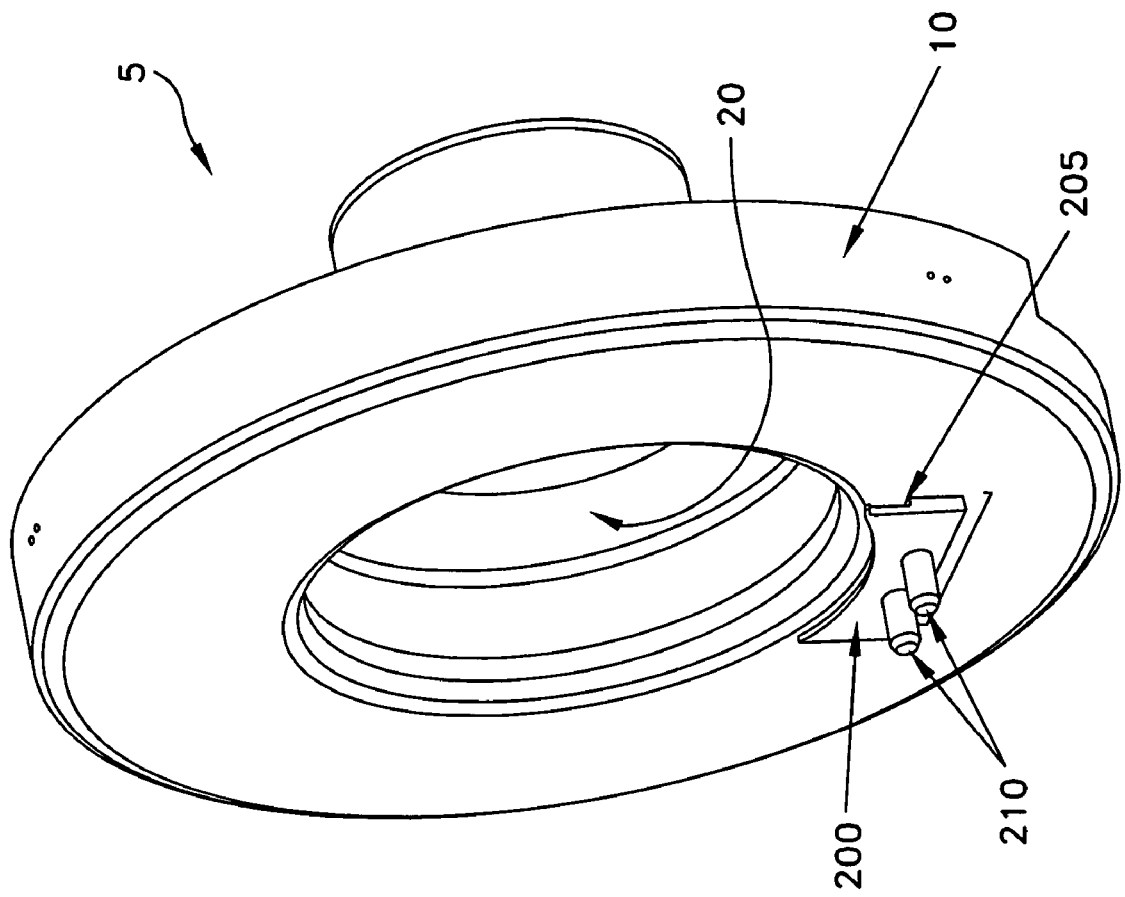
Figure 13:
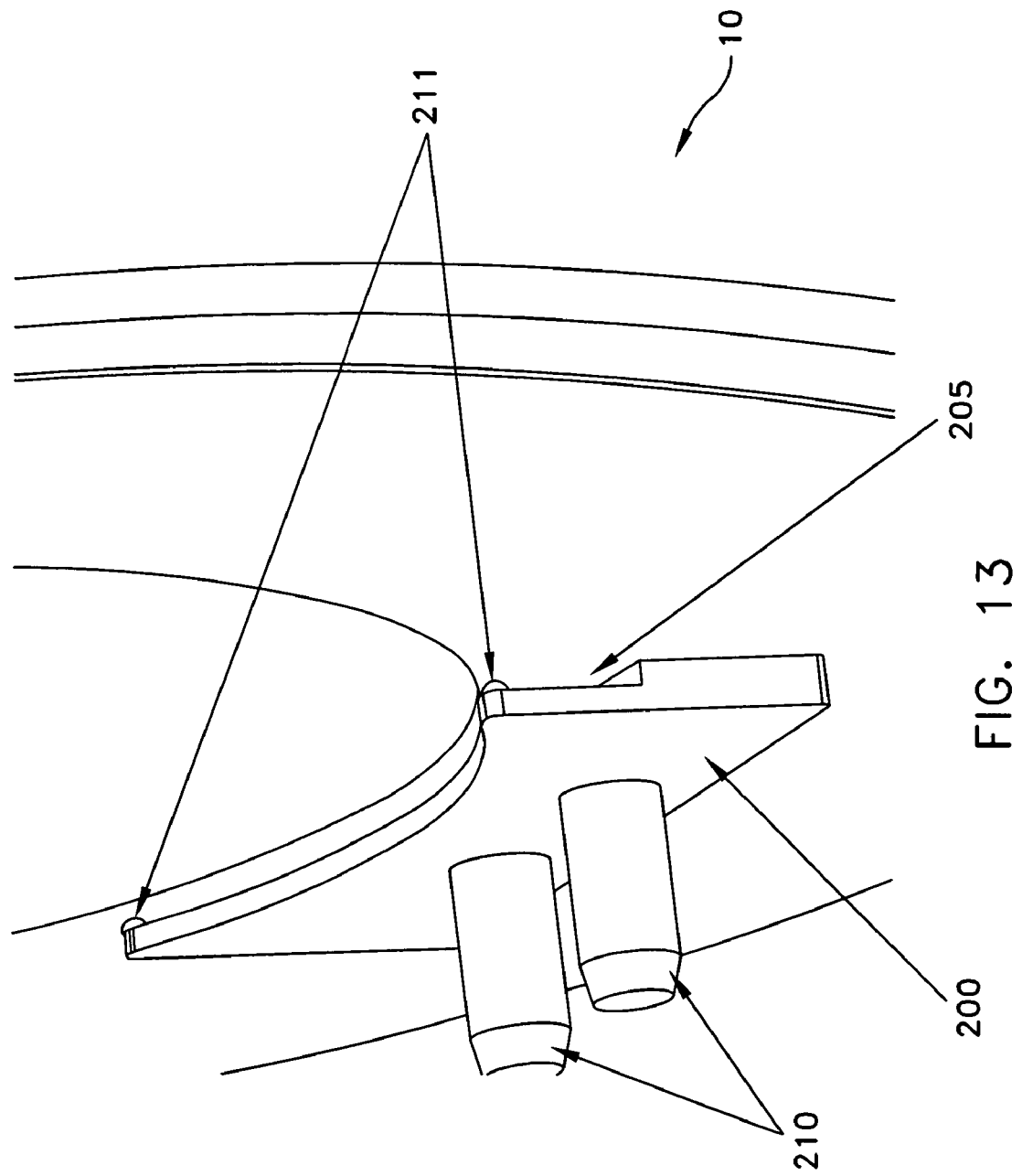
Figure 14:
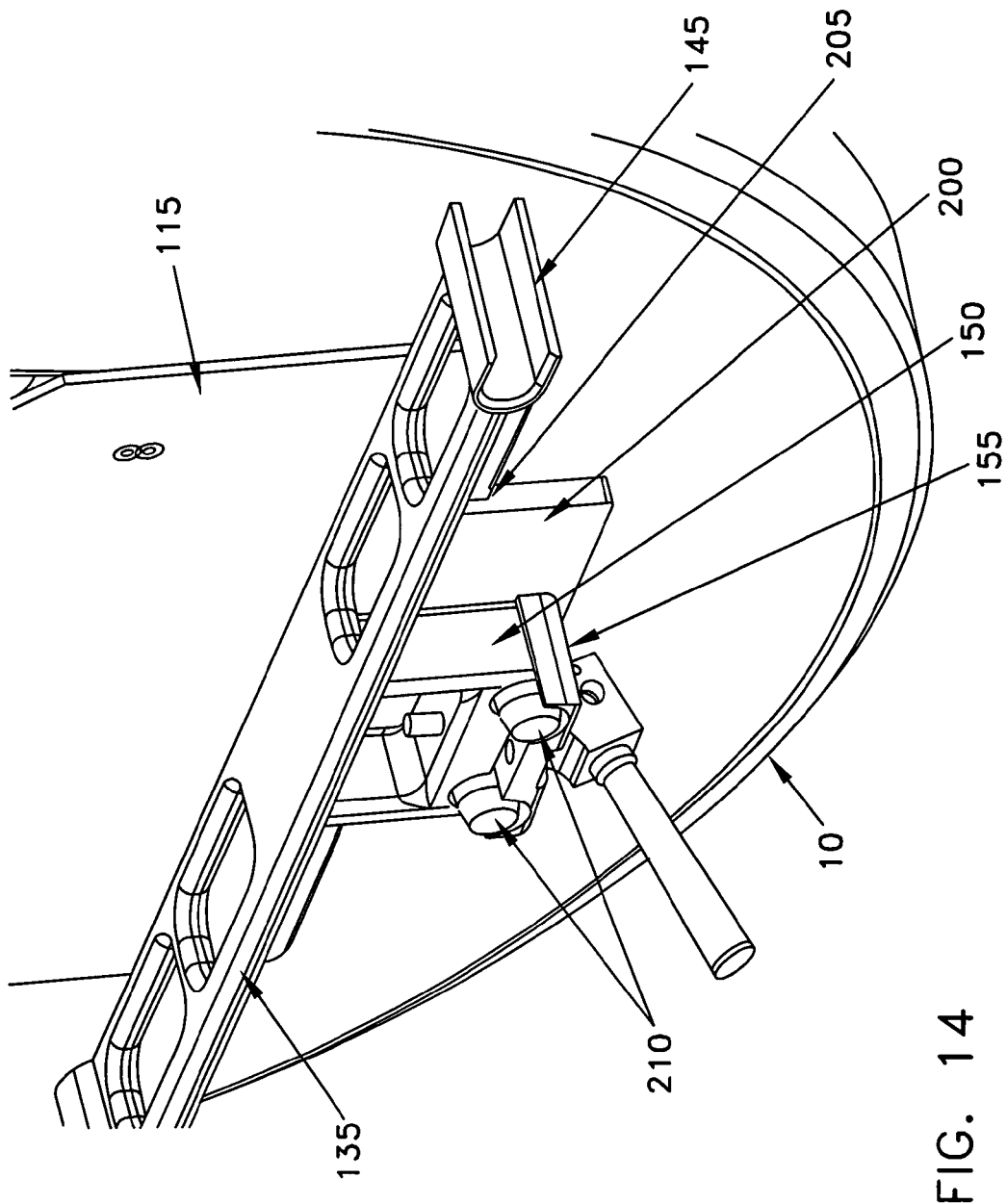
Figure 15:
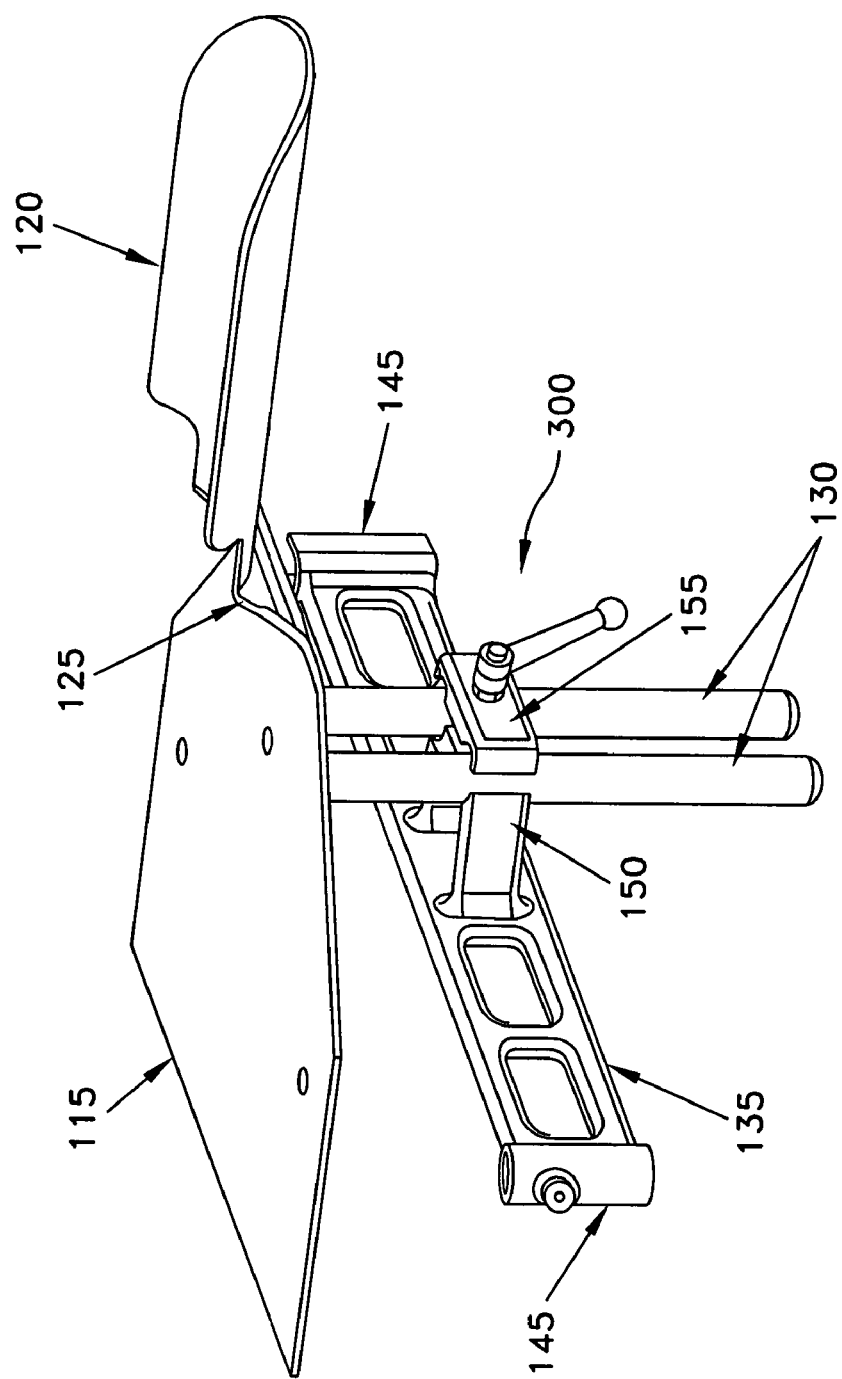
FIGS. 15-18 are schematic views showing an alternative form of riser clamp which may be used in connection with the present invention.
Figure 16:
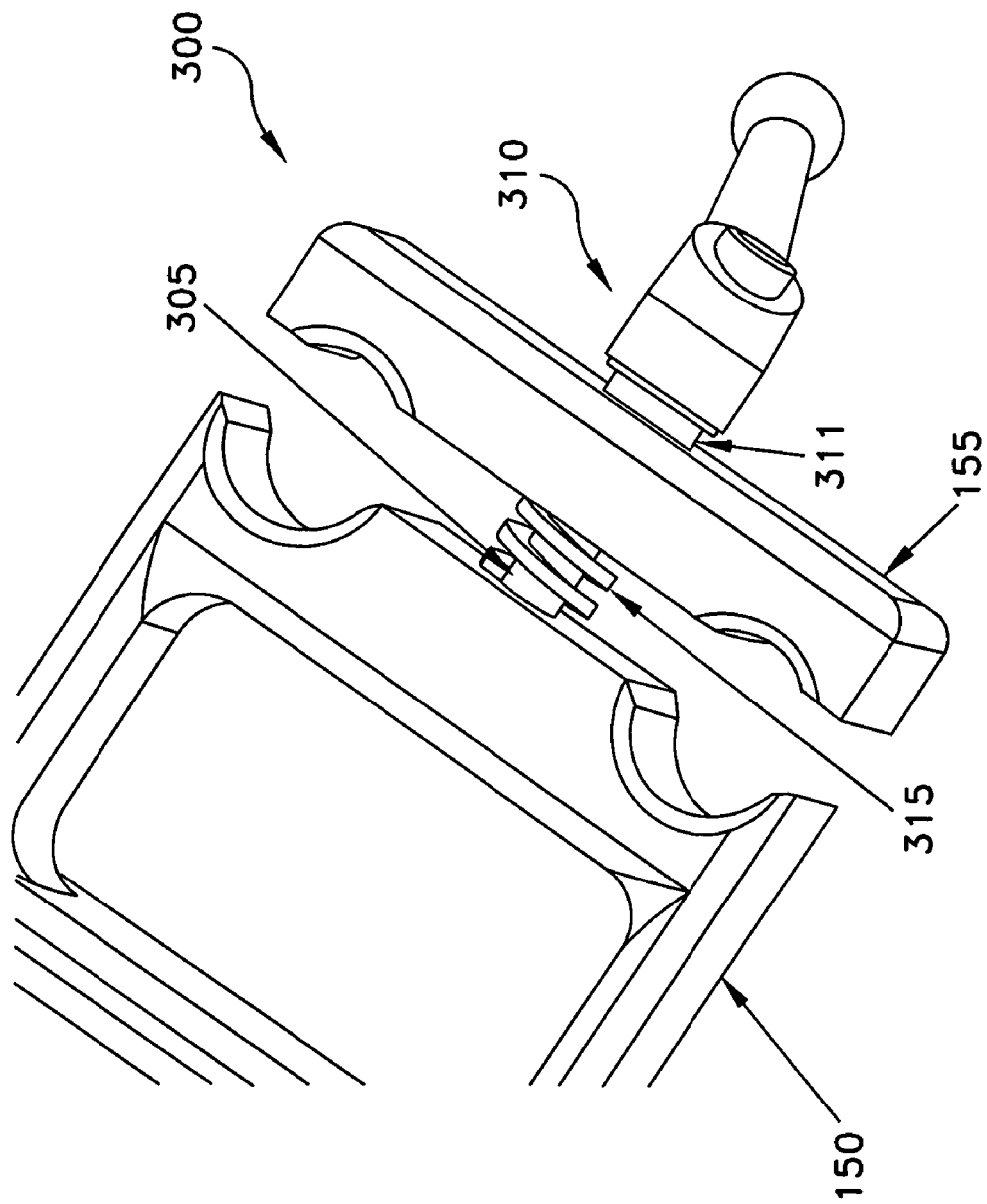
Figure 17:
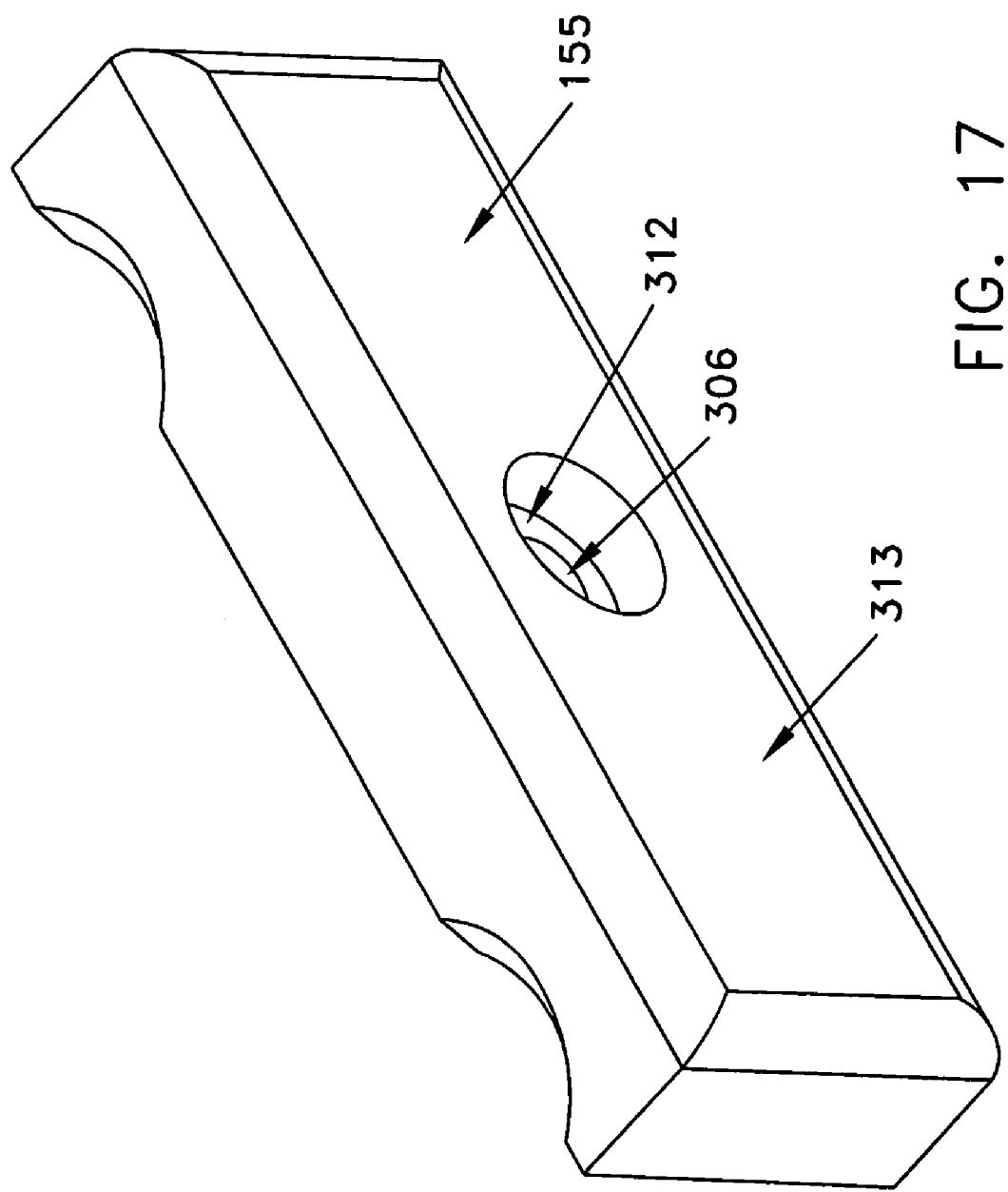
Figure 18:
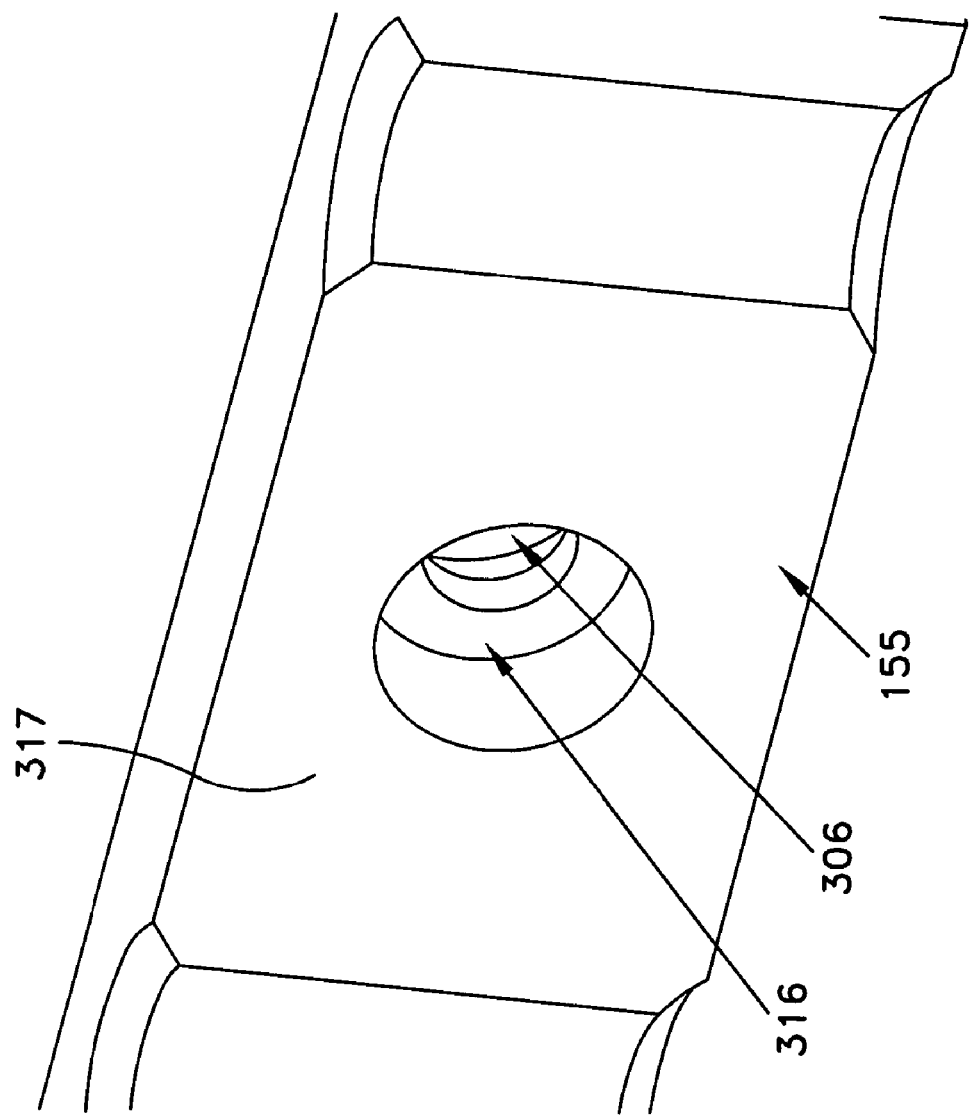

Looking next at FIGS. 11-14, CereTom™ CT machine 5 can be configured to facilitate storing extender 100 on torus 10 of CereTom™ CT machine 5. More particularly, a plate 200, including an undercut 205 and at least one post 210, is attached to the surface of torus 10. Preferably undercut 205 includes two or more beads 211 (FIG. 13) which extend from plate 200 toward CereTom™ CT machine 5. Beads 211 may be made of an elastomer, or a plastic, or a metal. When extender 100 is to be stored on CereTom™ CT machine 5, risers 130 of support 105 are positioned in center opening 20 of CereTom™ CT machine 5 (FIG. 11), and then shoulder section 115 is placed between undercut 205 and torus 10 (FIG. 14), with beads 211 helping to hold shoulder section 115 against torus 10. At the same time, the extender's head section 120 bears against the face of torus 10 (FIG. 11). Then adapter 110 is mounted on the at least one post 210 so as to press shoulder section 115 and head section 120 against torus 10 of CereTom™ CT machine 5 (FIGS. 11 and 14). This is done by opening riser clamp 140, mounting riser clamp 140 on the at least one post 210, and then closing riser clamp 140 so as to secure adapter 110 and hence extender 100 to CereTom™ CT machine 5. Thus it will be seen that the at least one post 210 is preferably arranged so as to have the same configuration as that of the at least one riser 130 (i.e., preferably posts 210 and risers 130 are similar in diameter and, where multiple risers 130 are provided, similar in number and spacing).

Alternative Riser Clamp Constructions

It should be appreciated that it is possible to provide a riser clamp having a construction which is different from the cam-operated riser clamp shown in FIGS. 7-10.

Thus, and looking now at FIGS. 15-18, a crank-operated riser clamp 300 is shown. Crank-operated riser clamp 300 generally comprises a screw 305 which has one end mounted in fixed plate 150 and another end passing through a bore 306 formed in movable plate 155. A crank 310 rides on the free end of screw 305. The inner portion 311 of crank 310 bears against an annular shoulder 312 formed in the outside face 313 of movable plate 155. A spring 315 biases movable plate 155 away from fixed plate 150; one end of spring 315 bears against fixed plate 150 and the other end of spring 315 bears against an annular surface 316 formed in the inside face 317 of movable plate 155. As a result of this construction, crank 310 can be used, in conjunction with spring 315, to move movable plate 155 toward and away from fixed plate 150 so as to close and open riser clamp 300.

Alternative Adapter Constructions

As noted above, many different bed and gurney configurations exist in the marketplace, and hence many different configurations may be provided for bed and gurney mount 135, with the specific configuration of bed and gurney mount 135 being matched to the particular configuration of the bed or gurney BG with which the extender 100 is to be used.

Figure 19:
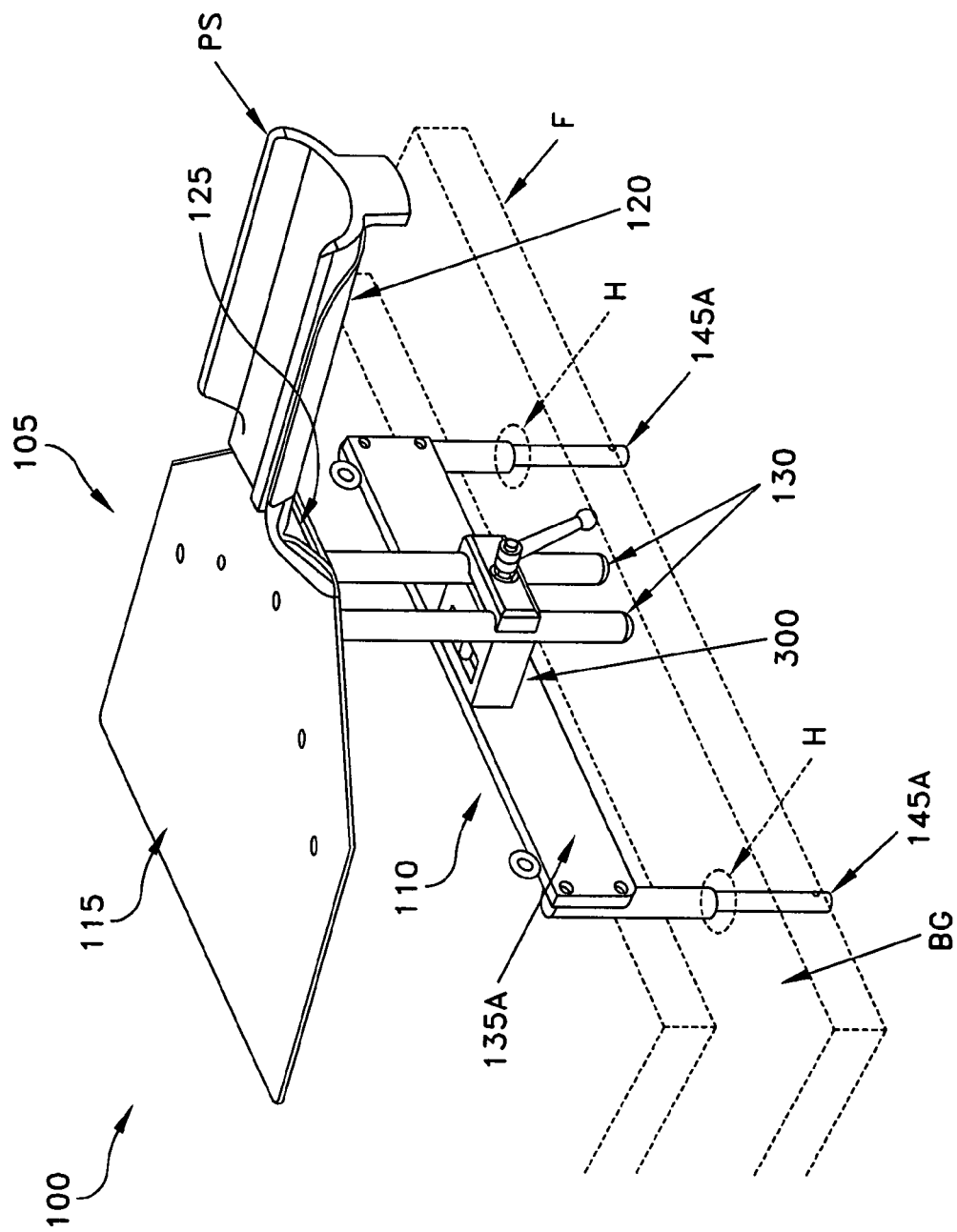
FIG. 19 is a schematic view showing an alternative form of the adapter portion of the bed and gurney extender.

Thus, for example, and looking now at FIG. 19, there is shown an alternative bed and gurney mount 135A. Bed and gurney mount 135A is generally similar to the bed and gurney mount 135 previously discussed, in the sense that the unit mounts to the bed or gurney BG and supports the crank-operated riser clamp 300 (which in turn mounts support 105). However, the alternative bed and gurney mount 135A shown in FIG. 19 is mounted to bed or gurney BG by fitting posts 145A into corresponding holes H formed in the frame F of bed or gurney BG.

If desired, a soft patient support PS may be added to bed and gurney support 105 so as to increase patient comfort. Thus, for example, and looking now at FIG. 19, a patient support PS is shown covering head section 120 and neck section 125. Patient support PS may also cover shoulder section 115 if desired.

Figure 20:
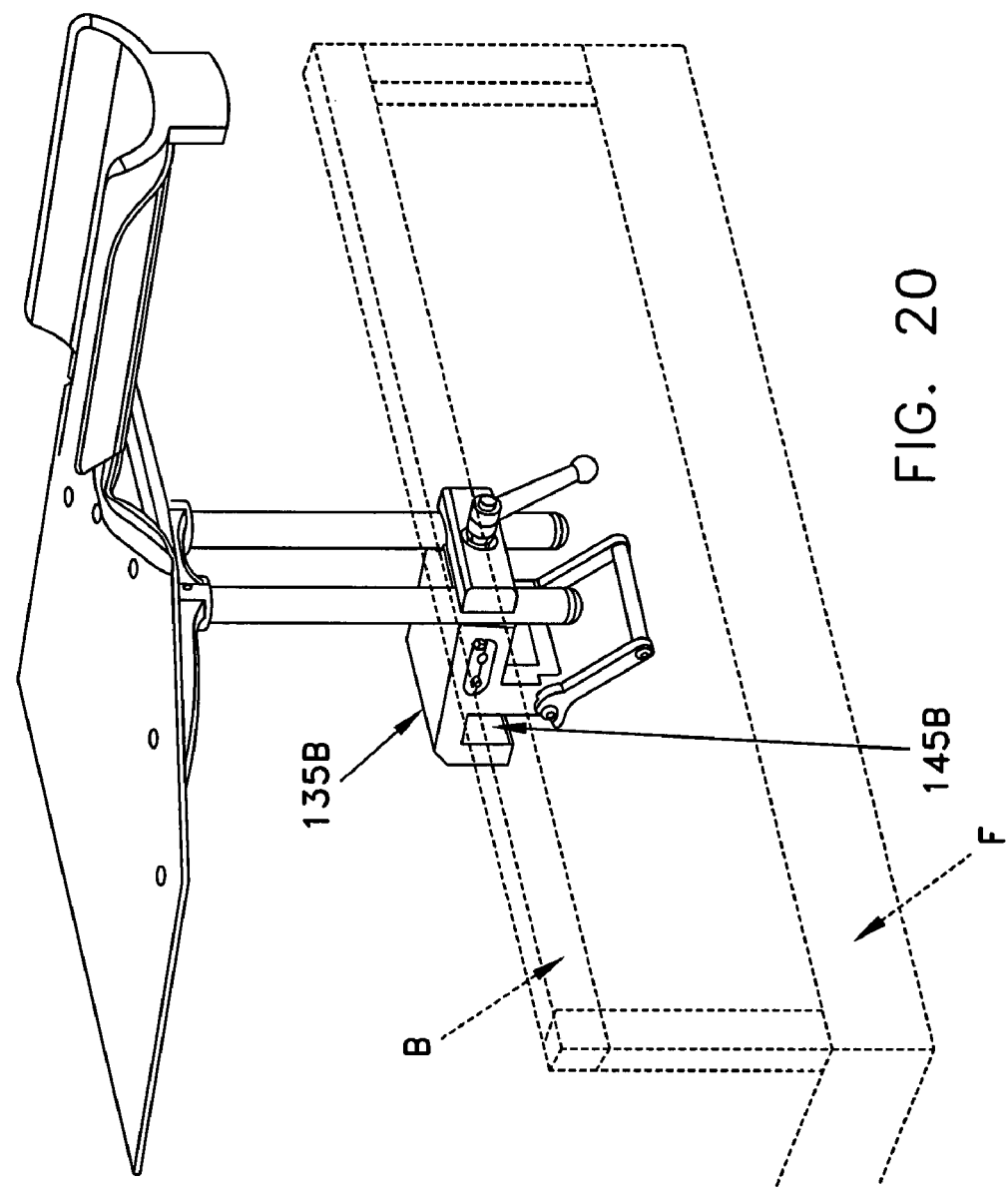
FIGS. 20 and 21 are schematic views showing still another alternative form of the adapter portion of the bed and gurney extender.
Figure 21:
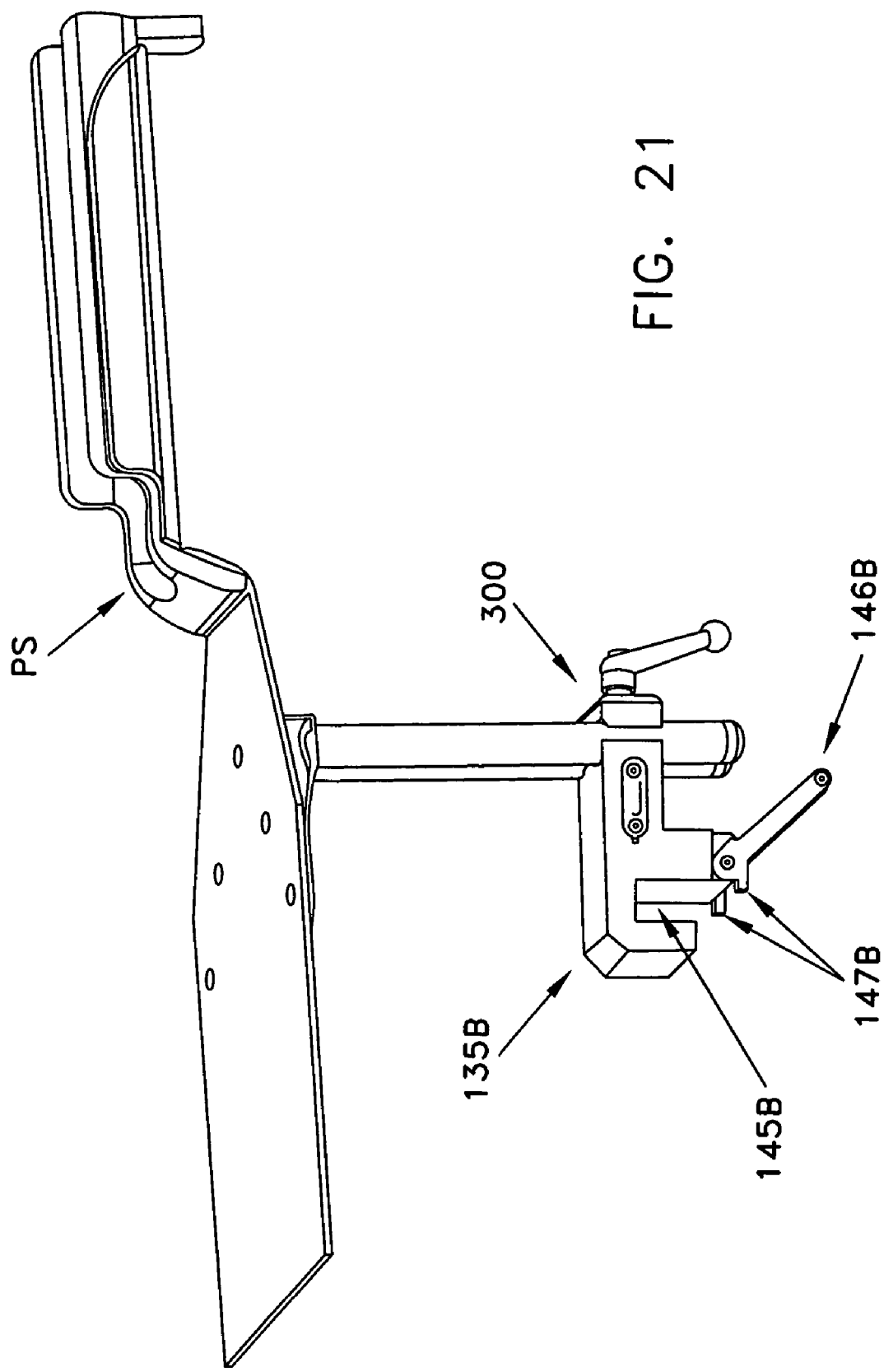

FIGS. 20 and 21 show another alternative bed and gurney mount 135B. Bed and gurney mount 135B generally comprises a rectangular bottom slot 145B which receives a rectangular horizontal bar B of frame F. Due to the rectangular profiles of bottom slot 145B and bar B, bed and gurney mount 145B will be rotationally stable relative to horizontal bar B. A lever latch 146B, including fingers 147B, releasably secures bed and gurney mount 135B to the rectangular horizontal bar B. Riser clamp 300 is formed integral with bed and gurney mount 135B.

Figure 22:
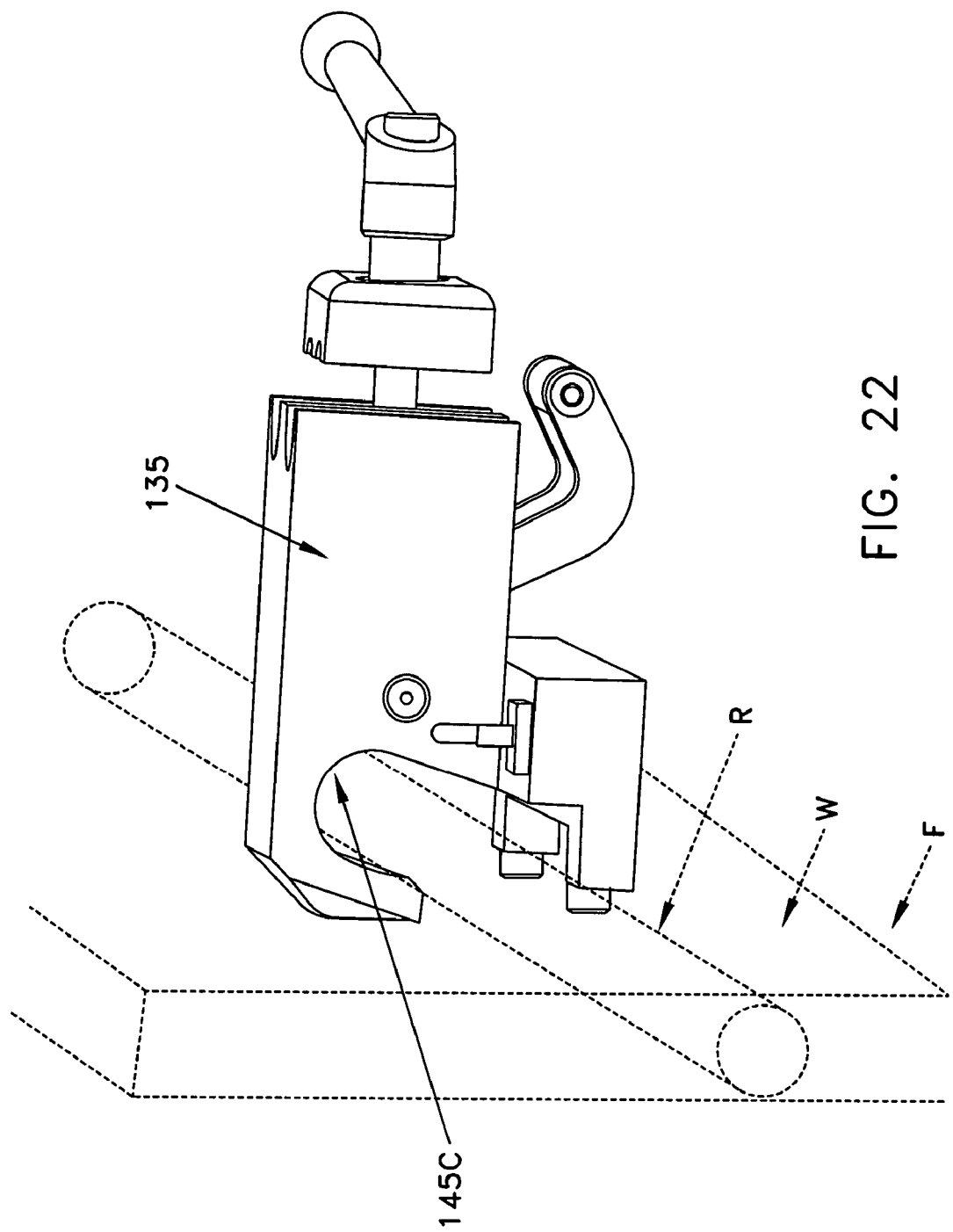
FIGS. 22 and 23 are schematic views showing yet another form of the adapter portion of the bed and gurney extender.
Figure 23:
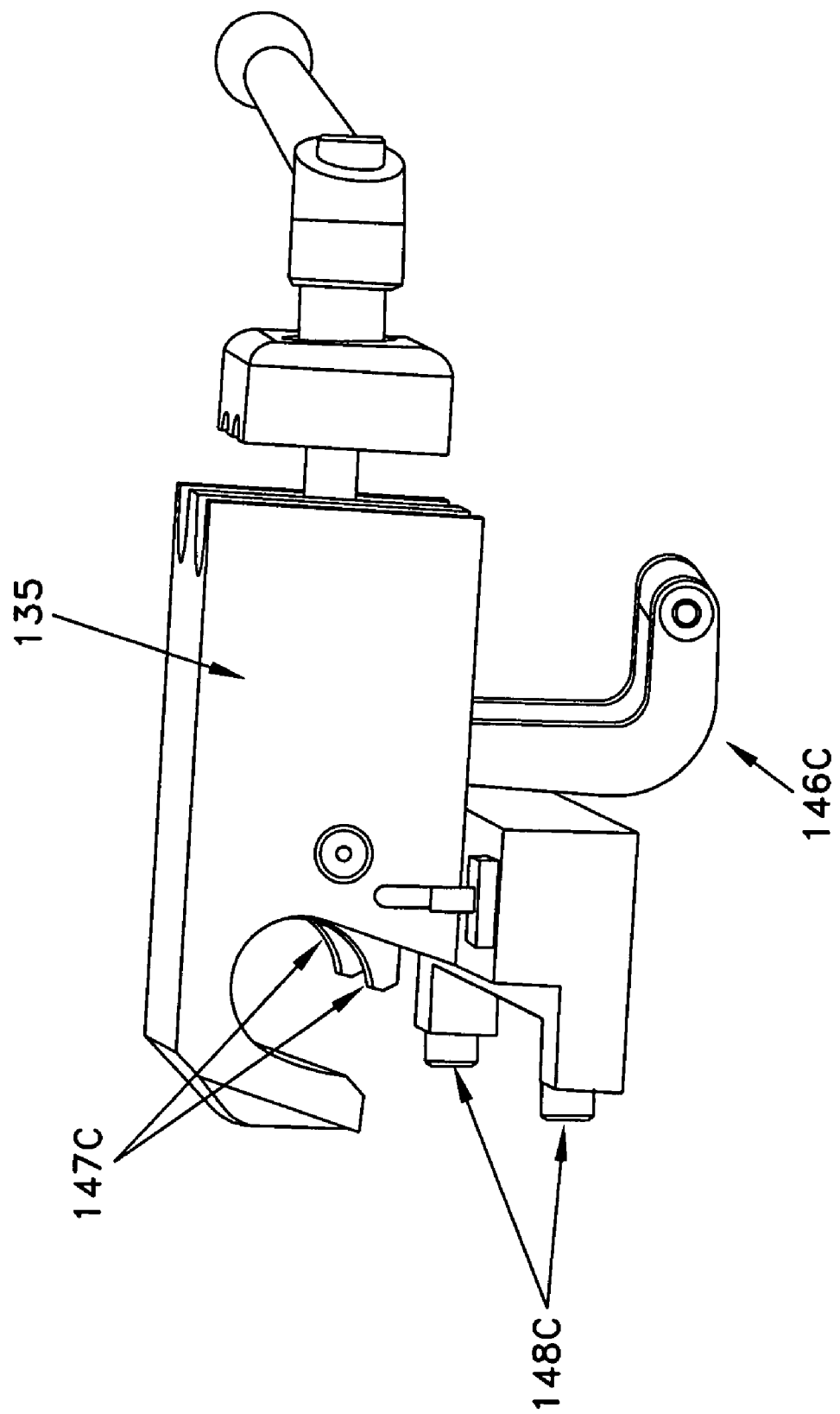

A slightly different arrangement is shown in FIGS. 22 and 23. More particularly, in some circumstances, the bed or gurney BG may comprise a frame F which includes a round rod R disposed adjacent to a vertical wall W. In this circumstance, rotational stability must be provided if riser clamp 300 is mounted to the round rod R. Accordingly, and looking now at FIGS. 22 and 23, there is shown a bed and gurney mount 135C having a slot 145C formed therein. A lever latch 146C, including fingers 147C, releasably secures bed and gurney mount 135C to the round rod R. A pair of feet 148C bear against wall W of frame F so as to prevent clockwise rotation (when seen from the angle of view of FIGS. 22 and 23) of bed and gurney mount 135C relative to round rod R. Riser clamp 300 is formed integral with bed and gurney mount 135C.

It is also possible to form extender 100 without using risers 130. More particularly, and looking now at FIG. 24, there is shown an extender 100D which generally comprises a shoulder section 115D and a head section 120D, joined by a neck section 125D. A horizontal rod 130D is used to connect extender 100 to adapter 110. In this construction, adapter 110 generally comprises a bed and gurney mount 135D for selective attachment to the frame F of the bed or gurney, and a clamp 400 for clamping horizontal rod 130D in position. Clamp 400 generally comprises a fixed jaw 405 and a movable jaw 410. A screw 415 secures movable jaw to 410 fixed jaw 405.

Alternative Bed and Gurney Extender Support

It should be appreciated that it is also possible to provide a bed and gurney support element having a construction which is different from bed and gurney support 105 shown in FIGS. 4-6.

Figure 25:
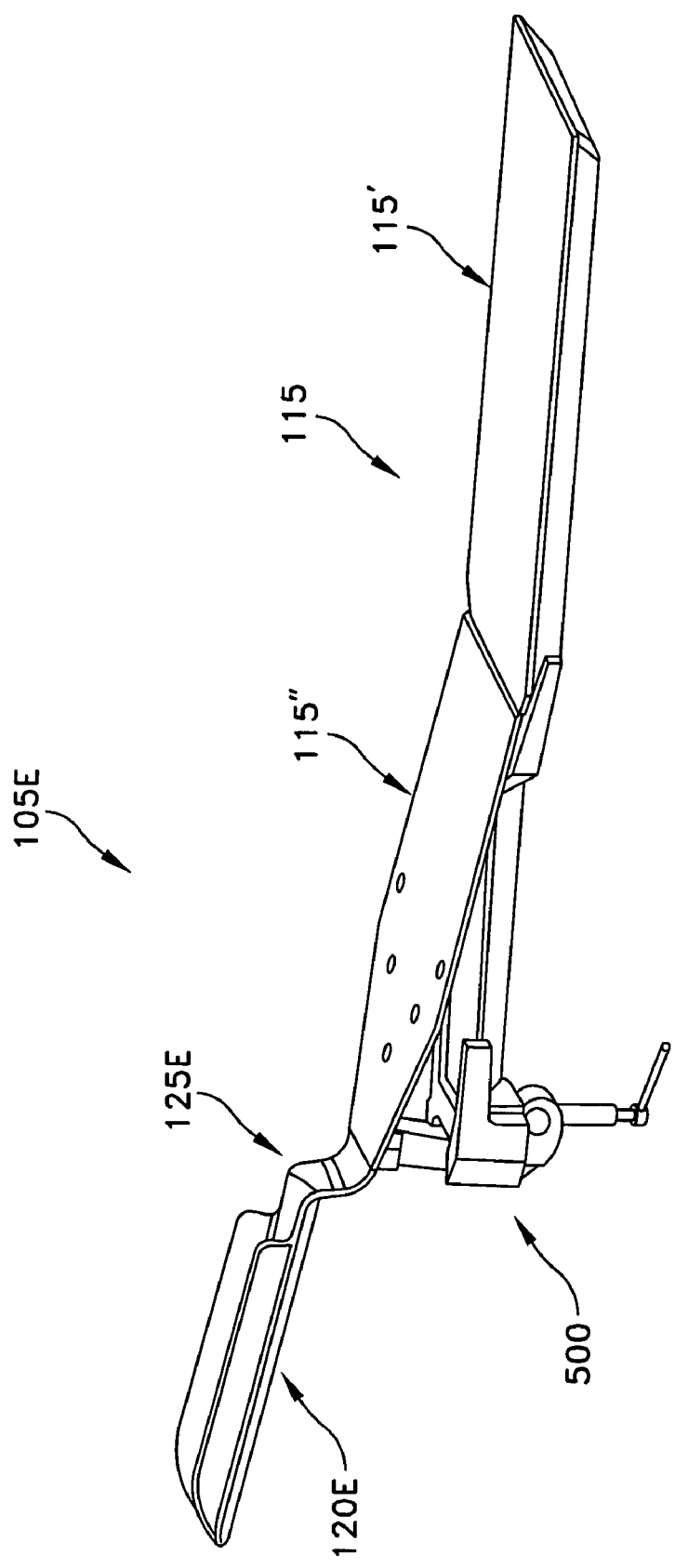
FIG. 25 is a schematic view showing another support formed in accordance with the present invention.

By way of example but not limitation, and looking now at FIG. 25, there is shown a support 105E which permits the patient's head to be aligned with the center opening 20 of CereTom™ CT machine 5. To that end, support 105E comprises a hinged shoulder section 115E for disposition under the shoulders of the patient, a head section 120E for supporting of the head of the patient, and a neck section 125E for connecting head section 120E to hinged shoulder section 115E. Hinged shoulder section 115E in turn a first shoulder section 115E' and a second shoulder section 115E". An elevator 500 is provided to raise or lower hinged shoulder section 115E" relative to hinged shoulder section 115E', whereby to permit the patient's head to be aligned with the center opening 20 of CereTom™ CT machine 5.

Figure 24:
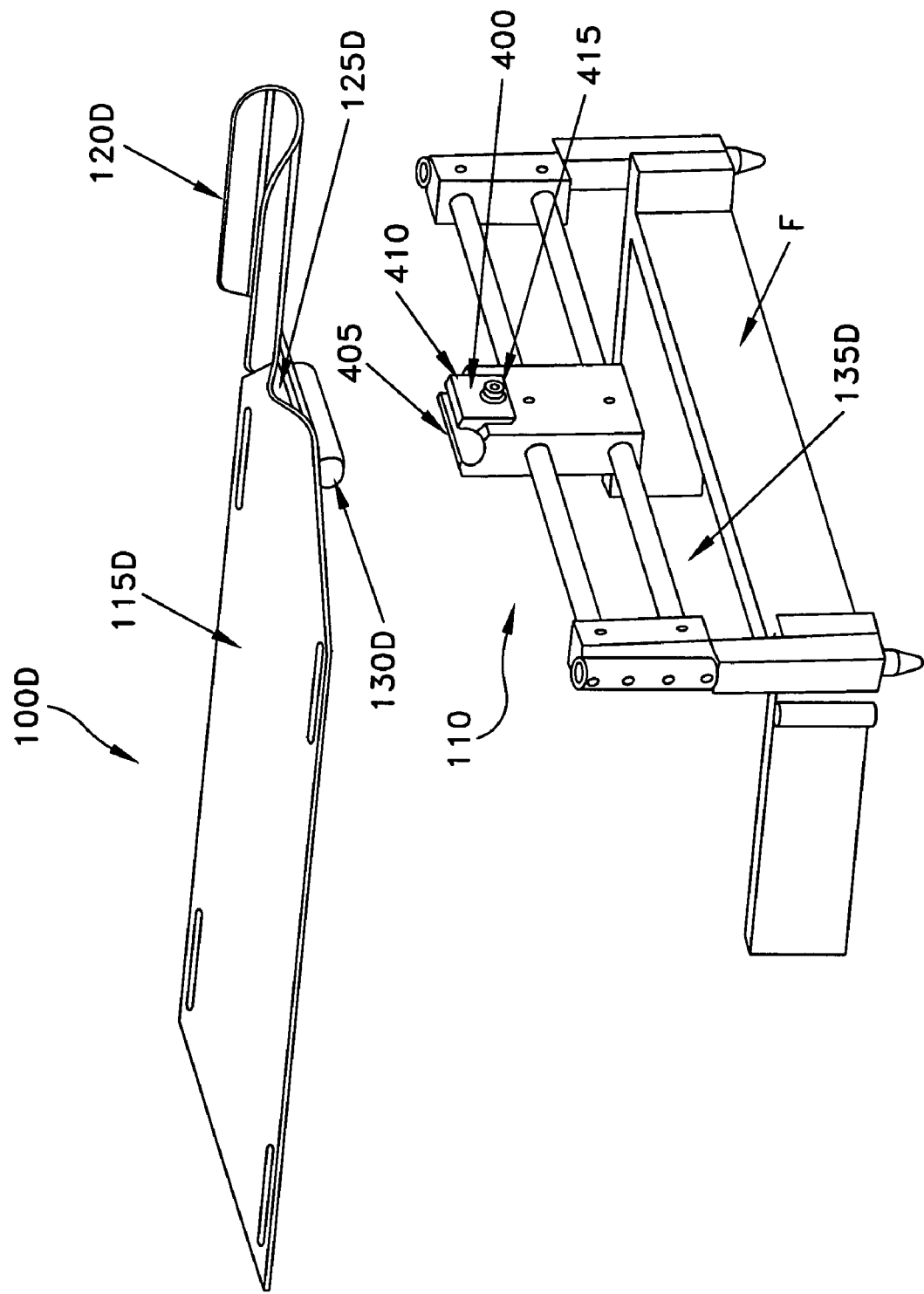
FIG. 24 is a schematic view showing another bed and gurney extender formed in accordance with the present invention.

Support 105E can be particularly useful when using an extender such as the extender 100D shown in FIG. 24, inasmuch as extender 100D does not provide vertical adjustment of extender 100D relative to the bed or gurney BG. Elevator 500 of support 105E can provide this vertical adjustment.

Application to Other Types of Scanning Systems

It should be appreciated that the present invention is not limited to use with a CereTom™ CT machine 5. It may be used with any type of CT machine where the CT machine is capable of moving its scan head relative to a fixed-position patient.

Furthermore, it should be appreciated that the present invention is not limited to use with CT machines. Thus, for example, the present invention may be used in connection with CT machines used for non-medical applications, e.g., with CT machines which are used to scan inanimate objects.

Furthermore, the present invention may be used with non-CT-type scanning systems.

Thus, for example, the present invention may be used with a nuclear medicine diagnostic apparatus such as that disclosed in U.S. Pat. No. 6,285,028, issued Sep. 4, 2001 to Yamakawa for SEMICONDUCTOR RADIATION DETECTOR AND NUCLEAR MEDICINE DIAGNOSTIC APPARATUS, which patent is hereby incorporated herein by reference, wherein the diagnostic apparatus moves on rails disposed on either side of the patient.

Of course, where the present invention is used in conjunction with scanners using something other than X-rays, it may be necessary to change the composition of head section 120 so that it is rendered transparent in the scanner.

In essence, the present invention has application to any type of mobile imaging system in which the patient (or object) must be scanned on their bed or gurney (or other support).

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A bed and gurney extender for selective attachment to a standard hospital bed or gurney for supporting the head of a patient during scanning, comprising:
    a support for supporting the head of the patient during scanning, wherein at least a portion of the support is X-ray transparent; and
    an adapter for selectively attaching the support to the bed or gurney;
    wherein the support comprises a shoulder section for disposition on the bed or gurney, under the shoulders of the patient, and a head section for supporting the head of the patient;
    wherein at least one riser extends out of the underside of the shoulder section;
    wherein the at least one riser is configured for selective attachment to the adapter; and
    wherein the adapter comprises a mount for selective attachment to the bed or gurney, and a riser clamp for selectively securing the at least one riser of the support to the adapter.

2. An extender according to claim 1 wherein the head section is connected to the shoulder section by a neck section.

3. An extender according to claim 1 wherein the head section is formed out of an X-ray transparent material.

4. An extender according to claim 3 wherein the X-ray transparent material is selected from the group consisting of carbon fiber and plastic.

5. An extender according to claim 1 wherein the head section is sized so as to fit within a scan opening of the scanning machine.

6. An extender according to claim 5 wherein the shoulder section is sized so as to be too large to fit within the scan opening of the scanning machine.

7. An extender according to claim 1 wherein the specific configuration of the mount varies according to the specific configuration of the bed or gurney.

8. An extender according to claim 1 wherein the mount comprises at least one opening for receiving at least one post provided by the bed or gurney.

9. An extender according to claim 8 wherein the mount comprises two openings for receiving two posts provided by the bed or gurney.

10. An extender according to claim 1 wherein the riser clamp comprises a fixed plate and a movable plate which together define at least one variably-sized opening.

11. An extender according to claim 10 wherein the at least one variably-sized opening is configured for selectively receiving and securing the at least one riser of the support.

12. An extender according to claim 10 wherein the riser clamp is configured to be cam-operated.

13. An extender according to claim 10 wherein the riser clamp is configured to be crank-operated.

14. An extender according to claim 1 wherein the support further comprises a soft patient support disposed atop the support.

15. An extender according to claim 1 wherein the mount comprises at least one post for inserting into at least one opening provided in the bed or gurney.

16. An extender according to claim 1 wherein the mount comprises two posts for inserting into two openings provided in the bed or gurney.

17. An extender according to claim 1 wherein the mount comprises a horizontally extending slot for receiving a portion of the frame of the bed or gurney.

18. An extender according to claim 17 wherein the horizontally extending slot has a round cross-section.

19. An extender according to claim 18 wherein the mount further comprises movable fingers for selectively engaging the portion of the frame of the bed or gurney, and further wherein the mount further comprises feet for selectively engaging a portion of the frame of the bed or gurney, whereby to selectively lock the mount to the frame of the bed or gurney.

20. An extender according to claim 17 wherein the horizontally extending slot has a rectangular cross-section.

21. An extender according to claim 20 wherein the mount further comprises movable fingers for selectively engaging the portion of the frame of the bed or gurney, whereby to selectively lock the mount to the frame of the bed or gurney.

22. Apparatus for use in scanning a patient on a bed or gurney, comprising:
a bed and gurney extender for selective attachment to a standard hospital bed or gurney for supporting the head of the patient during scanning, the extender comprising:
a support for supporting the head of the patient during scanning, wherein at least a portion of the support is X-ray transparent; and
an adapter for selectively attaching the support to the bed or gurney;
wherein the support comprises a shoulder section for disposition on the bed or gurney, under the shoulders of the patient, and a head section for supporting the head of the patient;
wherein at least one riser extends out of the underside of the shoulder section;
wherein the at least one riser is configured for selective attachment to the adapter; and
wherein the adapter comprises a mount for selective attachment to the bed or gurney, and a riser clamp for selectively securing the at least one riser of the support to the adapter.

23. Apparatus according to claim 22 wherein the apparatus further comprises a bed or gurney characterized by an attachment feature, and further wherein the adapter is configured to mate with the attachment feature.

24. Apparatus according to claim 22 wherein the apparatus further comprises a mobile scanner.

25. Apparatus according to claim 24 wherein the mobile scanner is a mobile CT machine.

26. Apparatus according to claim 25 wherein the mobile CT machine comprises a transport mechanism mounted to the base of the CT machine, wherein the transport mechanism comprises a fine movement mechanism for moving the CT machine precisely, relative to the patient, during scanning.

27. Apparatus according to claim 24 wherein the mobile scanner comprises at least one post, and further wherein at least a portion of the extender is configured for selected attachment to the at least one post whereby the extender can be selectively mounted to the mobile scanner.

28. Apparatus according to claim 22 wherein the apparatus further comprises a scanner which is movable relative to the bed or gurney.

29. Apparatus according to claim 28 wherein the scanner is movable on rails.

30. A method for scanning a patient, comprising:
mounting an extender to a bed or gurney of a patient so as to present the head of the patient on an X-ray transparent support remote from the remainder of the bed or gurney, the extender comprising:
a support for supporting the head of the patient during scanning, wherein at least a portion of the support is X-ray transparent; and
an adapter for selectively attaching the support to the bed or gurney;
wherein the support comprises a shoulder section for disposition on the bed or gurney, under the shoulders of the patient, and a head section for supporting the head of the patient;
wherein at least one riser extends out of the underside of the shoulder section;
wherein the at least one riser is configured for selective attachment to the adapter; and
wherein the adapter comprises a mount for selective attachment to the bed or gurney, and a riser clamp for selectively securing the at least one riser of the support to the adapter;
positioning the head of the patient adjacent to a scanning zone of a scanner; and
moving the scanner precisely relative to the patient during scanning while the head of the patient remains disposed on the X-ray transparent support.

* * * * *